(12) United States Patent
Edmonds et al.

(10) Patent No.: US 11,472,833 B2
(45) Date of Patent: Oct. 18, 2022

(54) NEUROACTIVE STEROIDS AND METHODS OF PREPARATION

(71) Applicant: Drawbridge Pharmaceuticals Pty Ltd, Malvern (AU)

(72) Inventors: Ian Edmonds, Vicksburg, MI (US); Edward J. Hessler, Vicksburg, MI (US)

(73) Assignee: DRAWBRIDGE PHARMACEUTICALS PTY LTD, Malvern (AU)

( * ) Notice: Subject to any disclaimer, the term of this patent is extended or adjusted under 35 U.S.C. 154(b) by 0 days.

(21) Appl. No.: 17/256,777

(22) PCT Filed: Jul. 3, 2019

(86) PCT No.: PCT/AU2019/050697
§ 371 (c)(1),
(2) Date: Dec. 29, 2020

(87) PCT Pub. No.: WO2020/006596
PCT Pub. Date: Jan. 9, 2020

(65) Prior Publication Data
US 2021/0355157 A1    Nov. 18, 2021

Related U.S. Application Data

(60) Provisional application No. 62/693,546, filed on Jul. 3, 2018.

(51) Int. Cl.
| | | |
|---|---|---|
| C07J 75/00 | (2006.01) | |
| B01J 23/46 | (2006.01) | |
| C07J 7/00 | (2006.01) | |
| B01J 23/44 | (2006.01) | |

(52) U.S. Cl.
CPC ............... *C07J 75/00* (2013.01); *B01J 23/44* (2013.01); *B01J 23/462* (2013.01); *C07J 7/002* (2013.01)

(58) Field of Classification Search
CPC ................. C07J 75/00; B01J 23/462
See application file for complete search history.

(56) References Cited

U.S. PATENT DOCUMENTS 2,647,134 A   7/1953   Hogg et al.
3,714,352 A   1/1973   Davis et al.

FOREIGN PATENT DOCUMENTS

| DE | 2030402 | 1/1971 |
|---|---|---|
| WO | WO 2011/088503 A1 | 7/2011 |
| ZA | 703861 B | 2/1971 |

OTHER PUBLICATIONS

International Preliminary Report on Patentability in PCT/AU2019/050697 dated Jan. 5, 2021.
Goodchild CS, et al., "Antinociceptive properties of neurosteroids IV: pilot study demonstrating the analgesic effects of alphadolone administered orally to humans," (2001) *British Journal of Anaesthesia*, 86: 528-534.
Goodchild CS, et al., "Prevention and Reversal of Morphine Tolerance by the Analgesic Neuroactive Steroid Alphadolone," (2009) *Pain Med*, 10: 890-901.
Nadeson, R. and Goodchild CS, "Antinociceptive properties of neurosteroids III: experiments with alphadolone given intravenously, intraperitoneally, and intragastrically," (2001) *British Journal of Anaesthesia*, 86: 704-708.
Winter L et al., "Antinociceptive Properties of Neurosteroids: A Comparison of Alphadolone and Alphaxalone in Potentiation of Opiod Antinociception," (2003) *Anesth Analg*, 97: 798-805.
Child et al., "The Pharmacological Properties in Animals of CT1341—A New Steroid Anaesthetic Agent," (1971) *British Journal of Anaesthesia*, 43: 2-13.
International Search Report in PCT/AU2019/050697, dated Sep. 11, 2019.
Browne, P.A., et al., "A Study of the Henbest Reduction: The Preparation of 3α-Hydroxy-5α-and 3β-Hydroxy-5β-steroids," J. Chem. Soc. (C) 1969, pp. 1653-.1659.
Hill, Christopher K. and Hartwig, John F., "Site-selective oxidation, amination and epimerization reactions of complex polyols enabled by transfer hydrogenation," Nature Chemistry, vol. 9: 1213-1221, Dec. 2017.
Zhang, Zonglei, et al., "First Synthesis of a C-Homosteroid from Pregn-4-ene-3,11,20-trione" Helvetica Chimica Acta, vol. 94: 98-104 (2011).
J. Von Euw, et al., 1994 "Über Bestandteile der Nebennierenrinde und verwandte Stoffe. 68. Mitteilung. Pregnandiol-(3α, 11α)-on-(20) und Pregnandiol-(3β, 11α)-on-(20)", Helvetica Chimica Acta, vol. 27, No. 1, pp. 821-839.
Phillipps, G.H., "Structure-activity relationships in steroidal anaesthetics", Journal of Steroid Biochemistry, Pergamon Press PLC, GB, vol. 6, No. 5, pp. 607-613 (1975).

*Primary Examiner* — Barbara P Badio
(74) *Attorney, Agent, or Firm* — Knobbe, Martens, Olson & Bear, LLP

(57) ABSTRACT

Neuroactive steroid anaesthetic agents, methods for their preparation and compositions comprising the same are disclosed. Also provided are scaled up and/or GMP methods for preparing neuroactive steroids, such as alfaxalone, alfadolone and alfadolone acetate.

16 Claims, 9 Drawing Sheets

NEUROACTIVE STEROIDS AND METHODS OF PREPARATION

REFERENCE TO RELATED APPLICATIONS

This application is a U.S. National Phase of International Application No.: PCT/AU2019/050697, filed Jul. 3, 2019, designating the U.S. and published in English on Jan. 9, 2020 as WO 2020/006596 A1, which claims priority to U.S. Provisional Patent Application No. 62/693,546 entitled "Neuroactive Steroids and Methods of Preparation" filed on 3 Jul. 2018, the entire content of which is hereby incorporated herein by reference.

FIELD

The present specification teaches neuroactive steroid anaesthetic agents, methods for their preparation and compositions comprising the same.

BACKGROUND

It has become increasingly apparent that the use of conventional anaesthetics to induce anaesthesia and sedation may result in long lasting disturbances and neuronal dysfunction. These include the induction of a state of neuroinflammation leading to cognitive impairment, apoptosis of immature oligodendrocytes, alterations in synaptic architecture and decreased neurogenesis amongst other events (Briner et al. (2010) *Anesthesiolgy* 112:546-556; Tan et al. (2009) *Chin. Med. J.* (Engl) 122:455-459; Zhu et al. (2010) *J. Cereb. Blood Flow Metabl* 30:1017-1030; Sanders et al. (2009) *Anesthesiology* 110:1077-1085).

While the brain has innate protective mechanisms against toxic xenobiotic substances (Selye (1971) *J Pharm Sci* 60:1-28), it is recognised that the innate protective mechanisms may be less efficient in the very young, elderly or subjects under stress such as following an acute illness, infection, chronic pain or surgery (Ek et al. (2010) *Toxicol Lett* 197:61-59).

Alfaxalone (also known as alphaxalone or 3α-hydroxy-5α-pregnane-11,20-dione) is a potent neuroactive steroid anaesthetic currently used in veterinary medicine (Child et al., *British Journal of Anaesthesia* 43:2-13, 1971).

Alfaxalone was widely used around the world as an intravenous anaesthetic together with alfadolone (also known as alphadolone or 3α,21-dihydroxy-5α-pregnane-11, 20-dione). This combination anaesthetic (also known as althesin; alfathesin) was used in human patients until 1983. Although these anaesthetics have a high therapeutic index, they were nevertheless withdrawn from clinical practice due to occasional, unpredictable yet severe anaphylactoid reactions to the polyethoxylated castor oil excipient (Cremophor EL) which formed part of the formulation for administration.

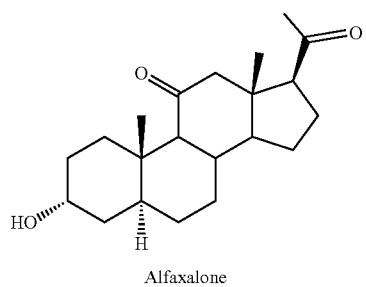

Alfaxalone

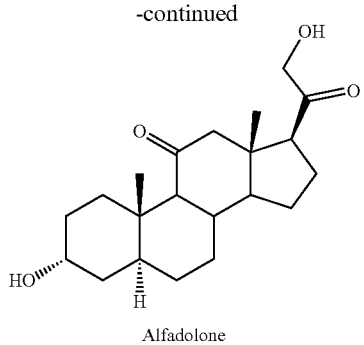

Alfadolone

Recently, a drug delivery system for neuroactive steroid anaesthetics has been described (refer to International Publication No. WO 2011/088503). Specifically, a host/guest complex formulation has been described comprising a neuroactive steroid anaesthetic and a cyclodextrin or modified form thereof which enables the administration of neuroactive steroid anaesthetics for use inducing anaesthesia or sedation in mammalian subjects. This host/guest drug delivery system enables the formulation and administration of neuroactive steroid anaesthetic without the use of the polyethoxylated castor oil excipient which was recognised to cause unpredictable, severe anaphylactoid reactions.

Furthermore, alternative routes of administration for neuroactive steroid anaesthetics have been described, including oral and or intraperitoneal routes of administration. For examples, refer to i) Goodchild C S, et al. *British Journal of Anaesthesia* (2001); 86:528-34; ii) Goodchild C S, et al. *Pain Med* (2009); 10:890-901; iii) Nadeson R and Goodchild C S. *British Journal of Anaesthesia* (2001); 86:704-8; and iv) Winter L et al. *Anesth Analg* (2003); 97:798-805, all of which are incorporated herein by reference in their entirety.

It is understood that alternative methods for formulation and/or routes of administration may overcome some of the deficiencies associated with neuroactive steroids including anaesthetics such as Althesin previously identified in human patients.

Despite new and effective methods for formulation and administration of neuroactive steroids, preparation of these complex steroids remains a challenge.

Previously described methods for the preparation of alfaxalone, such as that described in U.S. Pat. No. 3,714,352, suffer from low yields, lack selectivity, require extensive purification and/or are not readily scalable.

There is a need for new synthetic methods for the rapid preparation of neuroactive steroid anaesthetics in relatively few chemical steps, in high purity and/or which are industrially applicable. Additionally, there is a need for new stereoselective synthetic methods for the preparation of neuroactive steroids, especially stereoselective synthetic methods which may be applied on an industrial scale.

SUMMARY

The present invention is predicated in part on the identification of new methods for the synthesis of neuroactive steroid anaesthetics. In particular, the methods described herein provide for the regio and/or stereo selective functionalization of a steroid core. In one or more aspects, the processes of the present invention advantageously provide for the efficient preparation of neuroactive steroids in multigram, including kilogram-scale, quantities, in good to high yields. The processes disclosed herein are shown to be amenable to scale-up and allows production of compounds of Formula (I) and salts thereof on a large scale in an efficient and safe manner amenable to GMP conditions for the production of material suitable for medical administration.

Accordingly, in one or more aspects, the present invention provides a process for preparing a compound of Formula (I)

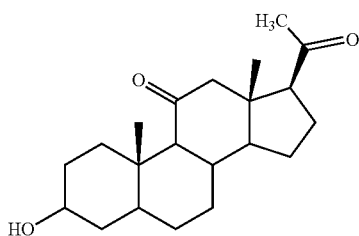

Formula (I)

comprising a ruthenium-catalyzed reduction of the 3-ketone of compound of Formula (II)

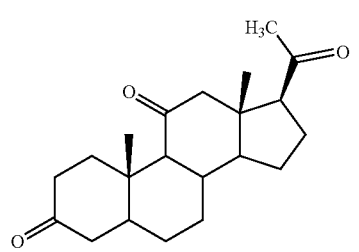

Formula (II)

to provide a compound of Formula (I).

In one or more embodiments, the compound of Formula (I) is 3α-hydroxy-5α-pregnane-11,20-dione of Formula (Ia):

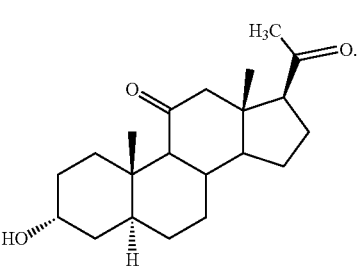

Formula (Ia)

In other aspects, the process of the present invention further comprises
i) reduction of 11α-hydroxyprogesterone of Formula (III)

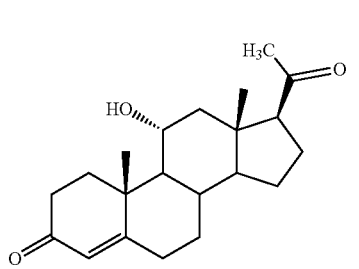

Formula (III)

to provide 11α-hydroxy-3,20-diketo-5α-H-pregnane of Formula (IV)

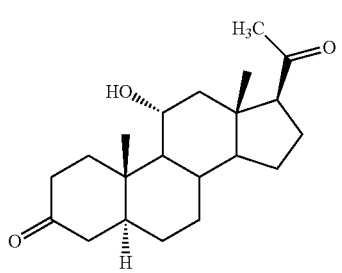

Formula (IV)

ii) oxidation of 11α-hydroxy-3,20-diketo-5α-H-pregnane to provide 3,11,20-triketo-5α-H-pregnane of Formula (II)

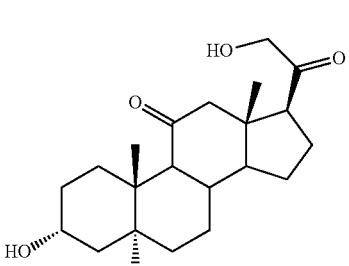

Formula (II)

iii) reduction of 3,11,20-triketo-5α-H-pregnane of Formula (II) to provide a compound of Formula (Ia).

In still other aspects, the process of the present invention further comprises iv) acetylation or hydroxylation of a compound of Formula (Ia) to provide a compound of Formula (V) or Formula (VI):

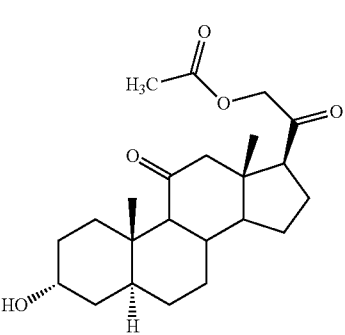

Formula (V)

Formula (VI)

In further aspects, the present invention provides compounds of Formula (Ia), Formula (V) or Formula (VI) prepared by the processes of the invention.

In other aspects, the present invention provides pharmaceutical, including anaesthetic compositions, comprising one or more neuroactive steroids prepared by the methods described herein.

The present disclosure also teaches the use of neuroactive steroids prepared by the methods described herein to induce neuroprotection of the central nervous system (CNS). The neuroactive steroids facilitate neuroprotection when either given in an anaesthetic or sedating formulation or as a non-sedating neuroprotectant formulation. By "neuroprotection" is meant the relieving, ameliorating, reducing or otherwise decreasing neuroinflammation and neuroinflammatory-promoting conditions.

DESCRIPTION

Figure 1:
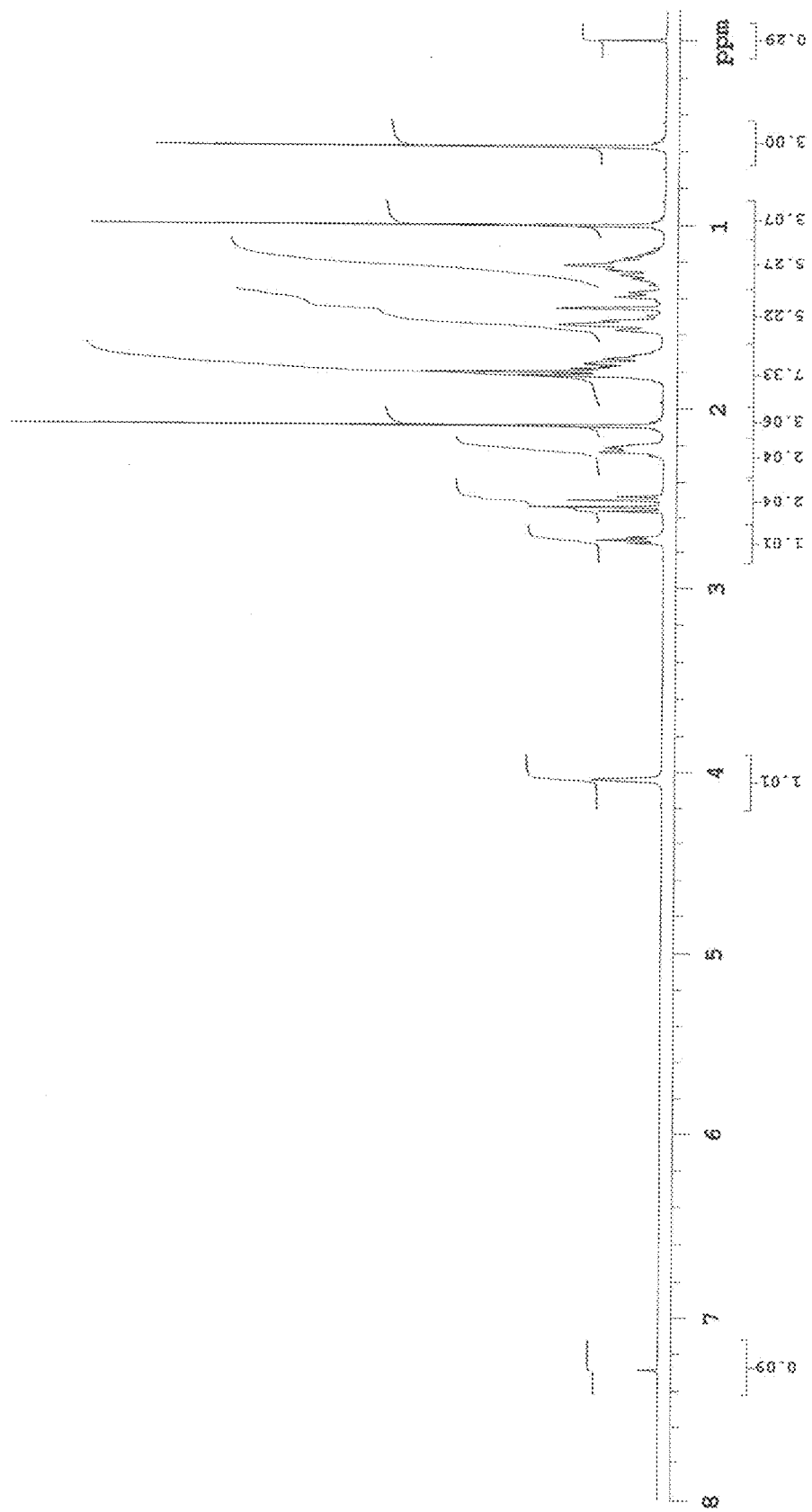
FIG. 1: $^1$H NMR spectrum of alfaxalone (3α-hydroxy-5α-pregnane-11,20-dione) prepared by the methods of the invention; at 25° C. in CDCl$_3$.

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a neuroactive steroid" includes a single neuroactive steroid, as well as two or more neuroactive steroids; reference to "an anaesthetic" includes a single anaesthetic, as well as two or more anesthetics; reference to "the disclosure" includes a single and multiple aspects taught by the disclosure; and so forth. Aspects taught and enabled herein are encompassed by the term "invention". All such aspects are enabled within the width of the present invention.

In its broadest sense, the term "neuroactive steroids" refers to naturally occurring or synthetic steroid compounds that have activity in the nervous system and/or are capable of modifying neural activity.

It is proposed to use anaesthetic/sedating formulations to induce anesthesia or sedation with minimal long term neuronal dysfunction or disturbance of neurocognitive function and which minimizes induction of neuroinflammation. Non-sedating formulations are also proposed for use as neuroprotecting formulations to reduce neuroinflammation and to increase transport of neurotoxins out of the CNS.

In one more aspects, the present invention advantageously provides improved processes for the synthesis of neuroactive steroids.

In one or more embodiments, the present invention advantageously provides improved processes for the synthesis of a compound generally represented by a compound of Formula (X):

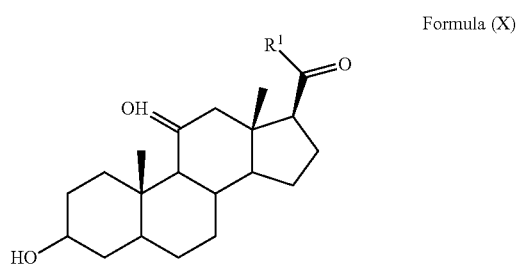

Formula (X)

wherein $R^1$ is $CH_3$ or $CH_2OH$ or $CH_2OC(O)CH_3$.

In one or more embodiments, the neuroactive steroid is alfaxalone (3α-hydroxy-5α-pregnane-11,20-dione); alfadolone (3α,21-dihydroxy-5α-pregnane-11,20-dione) or alfadolone acetate:

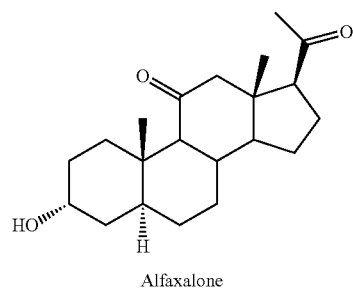

Alfaxalone

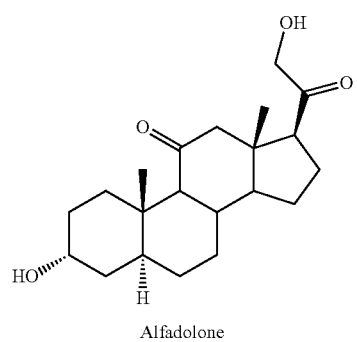

Alfadolone

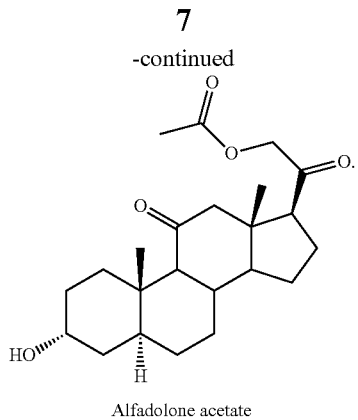

Alfadolone acetate

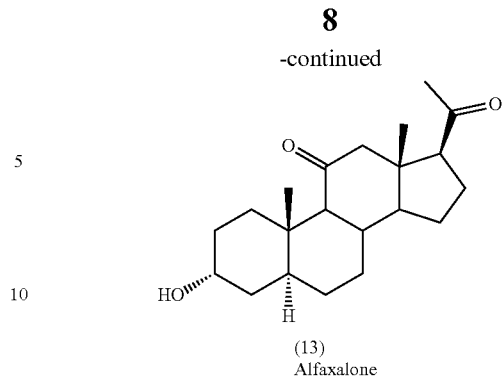

(13)
Alfaxalone

Representative synthesis for preparation of compound of alfaxalone of Formula (Ia) (13)

By way of example and without limitation, the process of the present invention may be further understood by reference to Scheme 1. Scheme 1 details a general synthetic process for preparation of alfaxalone (13), 3α-hydroxy-5α-pregnane-11,20-dione.

In one or more aspects, the processes of the present invention advantageously provide regioselective and/or stereoselective synthesis of neuroactive steroid anaesthetics.

In particular, it has surprisingly been found compounds of Formula (I) may be prepared by a regioselective ruthenium-catalyzed reduction of the 3-ketone of compound of Formula (II), as detailed in Scheme 2:

Scheme 1

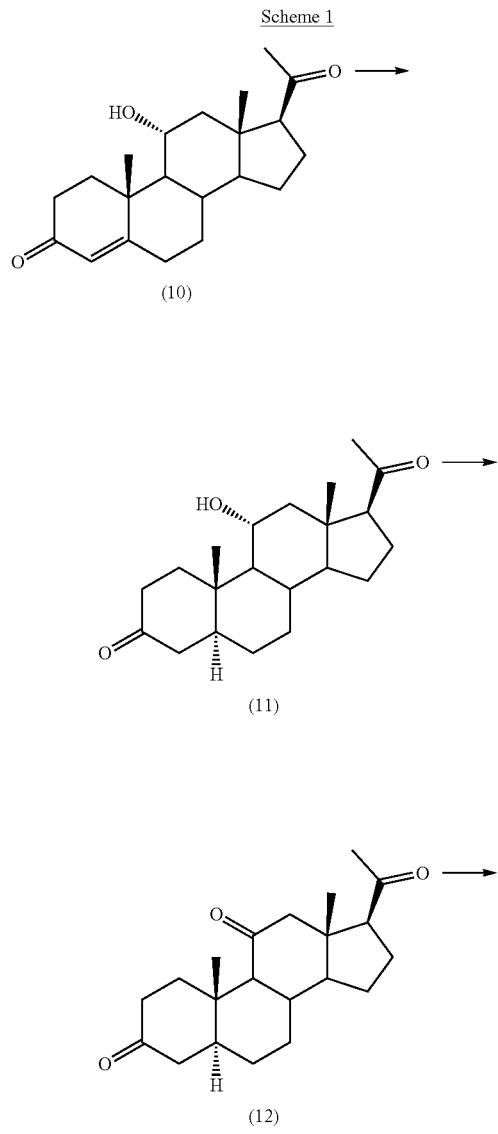

Scheme 2

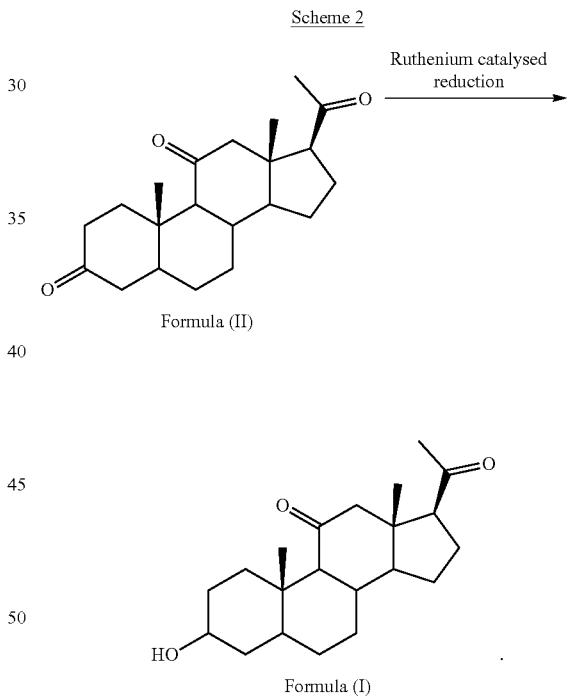

Ruthenium catalyzed reduction of compounds of Formula (II)

Surprisingly, the reduction is highly regioselective for the 3-ketone, over the ketones at positions 11 and 20 of compounds of formula (II). Such regioselectivity advantageously removes the need for protecting groups and as such enables the preparation of compounds of Formula (I), such as alfaxalone, in a reduced number of steps, thereby simplifying the overall synthesis.

In one or more aspects, the compound of Formula (I) is alfaxalone (3α-hydroxy-5α-pregnane-11,20-dione) as detailed in Scheme 3.

Scheme 3

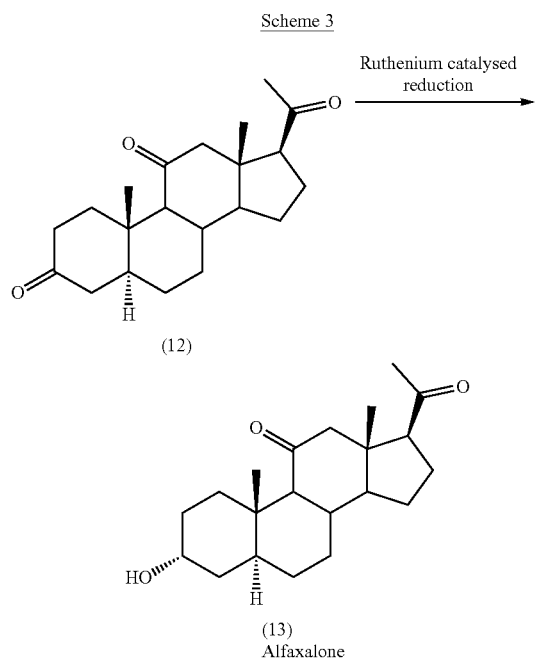

Ruthenium catalyzed reduction of 3,11,20-triketo-5α-H-pregnane (12) to provide alfaxalone (13)

In one or more aspects, the ruthenium catalyzed reduction is stereoselective for the 3α-hydroxy of Formula (I). In one or more embodiments, the ruthenium catalyzed reduction of 3,11,20-triketo-5α-H-pregnane provides ≥60:40; ≥66:34, ≥70:30, ≥75:25; ≥80:20; ≥81:19; ≥82:18; ≥83:17; ≥84:16; ≥85:15 stereoselectivity for the 3α-hydroxy:3β-hydroxy isomers of Formula (I).

In an embodiment, the ruthenium catalyzed reduction of 3,11,20-triketo-5α-H-pregnane provides ≥80:20 stereoselectivity for the 3α-hydroxy:3β-hydroxy isomers of Formula (I).

In one or more embodiments, the ruthenium catalyzed reduction of 3,11,20-triketo-5α-H pregnane provides ≥81:19, including ≥82:18, including ≥83:17, including ≥84:16, including ≥85:15 stereoselectivity for the 3α-hydroxy:3β-hydroxy isomers of Formula (I).

Such stereoselectivity advantageously removes the need for protecting groups and as such enables the preparation of compounds of Formula (I), such as alfaxalone, in a reduced number of steps, thereby simplifying the overall synthesis.

In one or more embodiments, the catalyst for the reduction of 3,11,20-triketo-5α-H pregnane is a suitable ruthenium catalyst. In particular, in one or more embodiments, the ruthenium catalyst is selected from the group consisting of RuCl(p-cymene)[(R,R)-Tsdpen], RuCl(p-cymene)[(S,S)-Tsdpen], RuCl(mesitylene)[(S,S)-Tsdpen], RuCl(p-cymene)[(S,S)-Fsdpen], and RuCl[(S,S)-Ms-DENEB]. In an embodiment, the ruthenium catalyst is RuCl(p-cymene)[(S,S)-Tsdpen].

In one or more embodiments, suitable amounts of the ruthenium catalyst are from about 0.005 to about 5.0 mole percent based on the number of moles of the substrate (i.e. compound of formula (II)). In particular, in one or more embodiments, the suitable amount of the ruthenium catalyst is from about 0.01 to about 2.0; including from about 0.02 to about 1.0 mole percent based on the number of moles of the substrate.

In one or more embodiments, the ruthenium catalyzed reduction of 3,11,20-triketo-5α-H-pregnane is carried out in the presence of a suitable base. In particular embodiments, the base is a potassium salt. In one or more embodiments, the base is selected from KHCO$_3$ and K$_2$CO$_3$. In some embodiments, the base is K$_2$CO$_3$.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature, unless the purpose of the solvent is to quench the reaction. A given reaction may be carried out in one solvent or a mixture of more than one solvent. Depending on the particular reaction step, suitable solvents for a particular reaction step may be selected independent of any other reaction step. In certain embodiments, the solvent is an anhydrous solvent. In still other embodiments, the solvent and/or reaction is under an inert atmosphere.

In one or more embodiments, the ruthenium catalyzed reduction of 3,11,20-triketo-5α-H-pregnane is carried out in the presence of an organic solvent. In particular embodiments, the solvent is a polar organic solvent. In one or more embodiments, the solvent is an alcohol solvent. In particular, the ruthenium catalyzed reduction is carried out in the presence of methanol (MeOH), ethanol (EtOH), isopropyl alcohol (IPA) or combinations thereof. In particular, the ruthenium catalyzed reduction is carried out in the presence of isopropyl alcohol (IPA).

In certain embodiments, the reduction is carried out at temperature in the range of about 25-35° C., including at a temperature in the range of about 20-30° C., including at approximately 25-27° C. In certain embodiments, the reduction is carried out over a period of about 5-25 hours, including 10-20 hours, including 12-18 hours, including over a period of about 16 hours.

In certain embodiments, the desired product may be purified by addition of additives such as magnesol, silica and carbon, filtered and condensed to provide the desired product.

In one or more embodiments, the stereoselectivity of the ruthenium-catalyzed reduction of 3,11,20-triketo-5α-H-pregnane (12) may be further improved by optional separation of the 3α and 3β isomers. It was advantageously found that the 3βOH isomer exhibits differing reactivity with bulky silylating agents, such as TBSCl, thereby facilitating resolution of the 3αOH and 3βOH isomers. In one or more embodiments, the 3αOH and 3βOH isomers may be optionally separated by selective reaction of 3αOH isomer with TBSCl to take advantage of the difference in reactivity of the axial and equatorial alcohols. Under these conditions, 3αOH remains largely unprotected. The TBS-protected 3βOH may then be separated from the desired 3αOH isomer by chromatography under standard conditions known in the art.

In one or more embodiments, the resultant product may be isolated and/or purified by methods known in the art. In certain embodiments, a thiol resin treatment and column chromatography may provide the desired product in high purity with low residual ruthenium. In other embodiments, the desired product may be purified by recrystallization.

In certain embodiments, the desired product may be further purified by recrystallization from a suitable organic solvent, such as IPA. Advantageously, such methods are scalable with good yields and very high purity. In certain embodiments, the purified product is ≥99% of the desired 3αOH isomer, and residual metals <1 ppm Pd and 1 ppm Ru. In certain embodiments, it is envisaged that such methods would advantageously meet GMP guidelines. In some embodiments, the purified product comprises less than 10 ppm, less than 9 ppm, less than 8 ppm, less than 7 ppm, less than 6 ppm, less than 5 ppm, less than 4 ppm, less than 3 ppm, less than 2 ppm, less than 1 ppm, or less than 0.5 ppm Ru; preferably less than 1 ppm Ru. In some embodiments, the purified product comprises less than 10 ppm, less than 9 ppm, less than 8 ppm, less than 7 ppm, less than 6 ppm, less than 5 ppm, less than 4 ppm, less than 3 ppm, less than 2 ppm, less than 1 ppm, or less than 0.5 ppm Pd; preferably less than 1 ppm Pd. In particular embodiments, the purified product comprises a combined concentration of less than 10 ppm, less than 9 ppm, less than 8 ppm, less than 7 ppm, less than 6 ppm, less than 5 ppm, less than 4 ppm, less than 3 ppm, less than 2 ppm, less than 1 ppm, or less than 0.5 ppm Pd and Ru; preferably less than 1 ppm Pd and Ru.

In one or more additional aspects, the present invention advantageously provides improved processes for the synthesis a compound of Formula (X), such as alfaxalone, by reduction of 11α-hydroxyprogesterone (10) to provide 11α-hydroxy-3,20-diketo-5α-H-pregnane (11), as detailed in Scheme 4. Oxidation of 11α-hydroxy-3,20-diketo-5α-H-pregnane (11) provides 3,11,20-triketo-5α-H-pregnane (12), as detailed in Scheme 5, which may subsequently be subjected to the described ruthenium-catalyzed reduction to provide a compound of Formula (X), such as alfaxalone (3α-hydroxy-5α-pregnane-11,20-dione, (13)).

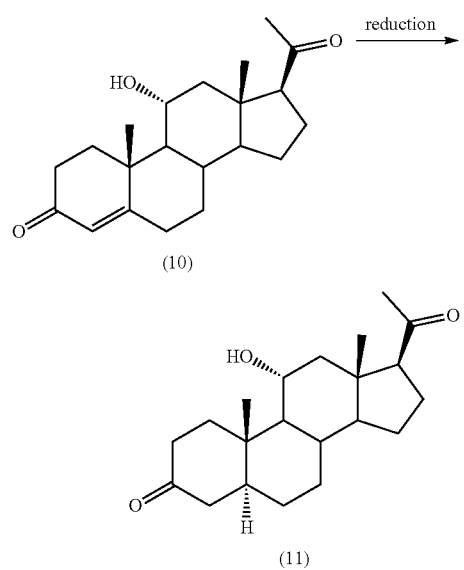

Reduction of 11α-hydroxyprogesterone (10) to 11α-hydroxy-3,20-diketo-5α-H-pregnane (11)

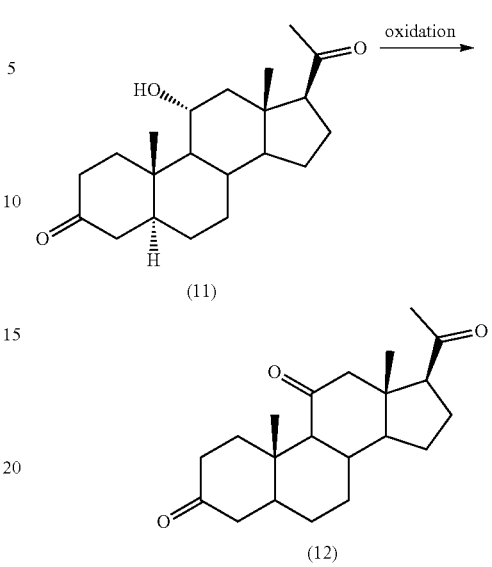

Oxidation of 11α-hydroxy-3,20-diketo-5α-H-pregnane (11) to 3,11,20-triketo-5α-H-pregnane (12)

In one or more embodiments, the present invention provides the hydrogenation of 11α-hydroxyprogesterone (10) with a suitable palladium catalyst. In particular, in one or more embodiments, the palladium catalyst is selected from the group consisting of Pd/CaCO$_3$, Pd/SrCO$_3$ and Pd/BaCO$_3$. In certain embodiments, the palladium catalyst is selected from the group consisting of 5% Pd/CaCO$_3$, 5% Pd/SrCO$_3$ and 5% Pd/BaCO$_3$. In an embodiment, the palladium catalyst for hydrogenation of 11α-hydroxyprogesterone is 5% Pd/CaCO$_3$.

In one or more embodiments, suitable amounts of the palladium catalyst are from about 0.01 to about 2.0 wt %; including from about 0.1 to about 1.0 wt %; including about 0.5 wt %.

In one or more aspects, the palladium catalyzed hydrogenation is stereoselective. Stereoselectivity advantageously simplifies the overall synthesis of compounds of Formula (I), such as alfaxalone, decreasing the number of synthetic steps, improving overall yield and/or reducing the need for complex purification and isolation procedures. In one or more embodiments, the palladium catalyzed hydrogenation of 11α-hydroxyprogesterone provides ≥75:25, ≥80:20, ≥85:15, ≥90:10, ≥95:5, ≥99.5:0.5, stereoselectivity for the 5αH:5βH isomers of 11α-hydroxy-3,20-diketo-5-H-pregnane. In certain embodiments, the palladium catalyzed hydrogenation of 11α-hydroxyprogesterone (10) provides 11α-hydroxy-3,20-diketo-5α-H-pregnane (11) in ≥99.5:0.5 stereoselectivity.

In one or more embodiments, the palladium catalyzed hydrogenation of 11α-hydroxyprogesterone is carried out in the presence of a suitable organic solvent. In one or more embodiments, suitable organic solvents include dichloromethane (DCM), a combination of dichloromethane and trimethylamine, or a combination of dichloromethane and triethylamine.

It is understood that the palladium catalyzed hydrogenation of 11α-hydroxyprogesterone is carried out in the presence of a hydrogen source, including H$_2$ gas. In certain embodiments, the hydrogenation is carried out at a pressure range 103-3447 kPa (15-500 psi). In an embodiment, the pressure is about 600 kPa (100 psi). In certain embodiments, the hydrogenation is carried out at temperature in the range of about 20 to about 40° C., including at approximately 30° C. In certain embodiments, the hydrogenation is carried out over a period of about 0.5 to about 6 hours, including about 1 to about 5 hours, including about 2 to about 4 hours, including over a period of about 3 hours.

The resultant product may be isolated and/or purified by methods known in the art. In certain embodiments, the reaction is cooled to approximately 20° C. and filtered and washed with DCM to remove the catalyst. In one or more embodiments, the DCM filtrate may be extracted by solvent extraction with 1.5M HCl, and 10% potassium bicarbonate. The aqueous phase may then be re-extracted with DCM, dried over an agent such as magnesium sulfate, filtered and condensed. In one or more further embodiments, the isolated product may be further purified by addition of tert-butyl methyl ether (MTBE) to form a slurry at a temperature in the range of 45-55° C., including about 50° C., for approximately 2 hours, then at a temperature in the range of 15-25° C., including about 20° C., for approximately 1 hour, to provide a crystalline slurry which may be filtered and dried to give the desired product. In certain embodiments, the desired product may be further purified by recrystallization from a suitable organic solvent, such as acetonitrile. Advantageously, such methods are scalable with good yields and very high purity. In certain embodiments, the purified product is ≥99% of the desired 5αH isomer and residual metals <1 Pd ppm. In certain embodiments, it is envisaged that such methods would meet GMP guidelines.

As noted above, in one or more embodiments, the present invention provides oxidation of 11α-hydroxy-3,20-diketo-5α-H-pregnane (11) to 3,11,20-triketo-5α-H-pregnane (12). In one or more embodiments, the oxidation is carried out in the presence of a suitable oxidant. In particular, the oxidation of 11α-hydroxy-3,20-diketo-5α-H-pregnane (11) is carried out in the presence of NaOCl, including NaOCl.5H$_2$O, optionally in the presence of one or more phase transfer catalysts. In one or more embodiments, the oxidation of 11α-hydroxy-3,20-diketo-5α-H-pregnane (11) is carried out in the presence of NaOCl.5H$_2$O with Bu$_4$NHSO$_4$ as a phase transfer catalyst under suitable conditions. In one or more embodiments, NaOCl.5H$_2$O is added portion-wise over a period of ≥0.5 hour, including ≥1 hour, including ≥2 hours, including ≥3 hours, including ≥4 hours.

It is understood that the oxidation of 11α-hydroxy-3,20-diketo-5α-H-pregnane (11) to 3,11,20-triketo-5α-H-pregnane (12) is carried out in the presence of a suitable organic solvent, including DCM.

In certain embodiments, the oxidation is carried out at temperature in the range of about 15-30° C., including at approximately 20-25° C. In certain embodiments, the oxidation is carried out over a period of about 1-7 hours, including 2-6 hours, including 3-5 hours before being cooled to a temperature in the range of about 5-20° C., including in the range of about 10-15° C., including approximately 12° C. before the reaction is quenched by addition of a suitable reducing agent, including a mild reducing agent, such as Na$_2$S$_2$O$_3$.

The resultant product may be isolated and/or purified by methods known in the art. In certain embodiments, the desired product may be isolated by solvent extraction using a suitable organic solvent, such as DCM, dried over an agent such as magnesium sulfate, filtered and condensed. In one or more further embodiments, the isolated product may be further purified by trituration and/or recrystallization with a suitable solvent, such as acetonitrile. In one or more embodiments, the desired product may be further purified by column chromatography to provide the desired product in good yield and high purity.

It is understood that compounds prepared by the processes of the invention may be isolated and/or purified by methods known in the art, including chromatographic processes.

As used herein, the term "isolated" when referring to a compound or intermediate refers to the compound or intermediate being physically removed from any other compound, solvent or substance or the act of physically removing any other compound, solvent or substance. As used herein, the reference to a "purification" step is distinct from an "isolation" step, with only completion of the latter providing a compound or intermediate in an isolated form, and completion of the former providing a compound or intermediate in the presence of at least one other compound, solvent or other substance. For instance, a purification step may involve steps such as washing with an aqueous or organic solvent, acid-base extraction, simple filtration or solvent swaps. This is to be contrasted with chromatographic separation steps, for example, flash column chromatography, liquid chromatography and other preparative chromatography methods, which provide the compound in a substantially pure form.

Advantageously, the present invention is contemplated to be practiced on at least a multigram scale, including a kilogram scale, including multikilogram scale, including an industrial scale. Multigram scale, as used herein, includes the scale wherein at least one starting material is present in 10 grams or more, including at least 50 grams or more, including at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

In one or more aspects, the processes of the present invention are advantageously in accordance with good manufacturing practices (GMP). GMP are understood as manufacturing practices required to conform to the guidelines recommended by agencies that control the authorization and licensing of the manufacture and sale of food and beverages, pharmaceutical products, supplements, medical devices and the like. Such agencies include the US Food and Drug Administration, the European Union GMP and the World Health Organisation (WHO). As such, the processes of the present invention advantageously provide neuroactive steroid anaesthetics in accordance with GMP guidelines, such that manufacturing, testing, and quality assurance of the resultant product is safe for human consumption or use.

Furthermore, it is generally recognised that alfaxalone (3α-hydroxy-5α-pregnane-11,20-dione) may be elaborated to alfadolone acetate and alfadolone by previously described methods as, for example, detailed in Scheme 6

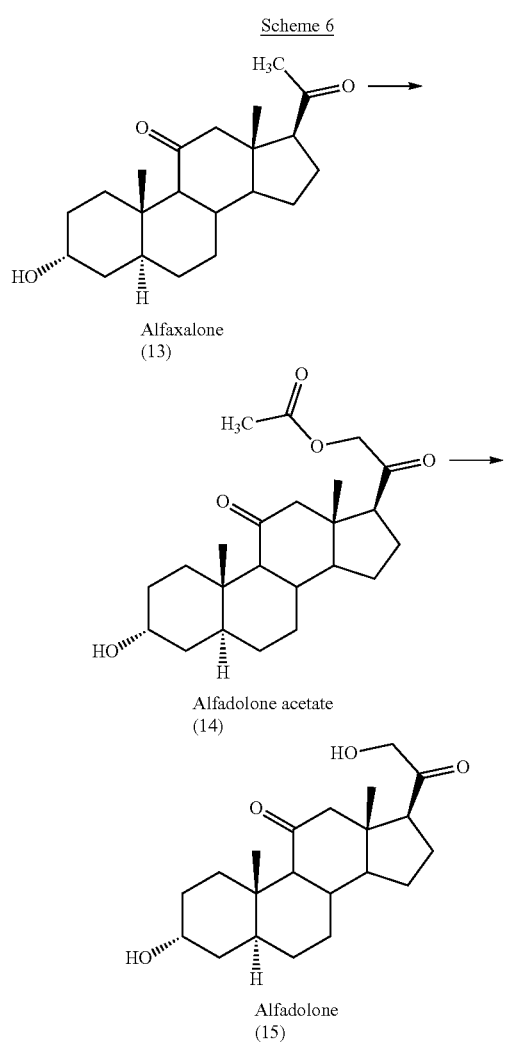

Scheme 6

Alfaxalone (13)

Alfadolone acetate (14)

Alfadolone (15)

Preparation of alfadolone and alfadolone acetate from alfaxalone

The process of the invention for the efficient preparation of neuroactive steroids in multigram, including kilogram-scale, quantities, in good to high yields. To achieve efficient synthesis, many of the steps are regio- and/or stereo-selective and avoid the use of complex protecting group strategies and/or unnecessary functional group interconversions. However, it is envisaged that in the preparation of the compounds of Formula (X) or a solvate thereof it may nevertheless be necessary and/or desirable to protect one or more sensitive groups in the molecule to prevent undesirable side reactions. The protecting groups used in the preparation of the compound of Formula (X) may be used in a conventional manner. See for example Protective Groups in Organic Chemistry, Ed. J. F. W. McOmie, Plenum Press, London (1973) or Protective Groups in Organic Synthesis, Theodora Green, John Wiley and Sons, New York (1981).

As used herein, "good" yields refer to yields which are viable for multigram process, including industrial process. For example, a good yield may be ≥50%, including ≥55%, including ≥60%, including ≥65%, including ≥70%, including ≥75%, including ≥80%, including ≥85%, including ≥90%, including ≥95%.

It is understood that the compounds of the present invention may exist in one or more stereoisomeric forms (e.g. enantiomers, diastereomers). Specific stereoisomeric forms are indicated as appropriate. Where specific stereoisomers are not indicated, the invention may encompass one or more isomers.

In certain embodiments, the process produces a compound of Formula (I). In other embodiments, the process produces a compound of Formula (I) or a salt thereof. In this regard, the salt may be a pharmaceutically acceptable salt. For example, physical properties of the compound such as pKa, pH, molecular mass, melting point, density, solubility, polarity, and appearance, and chemical properties such as degradation profile, reactivity, stability, and isomerism need to be considered, not only for handling during the method process, but also to ensure that the compounds remain active when formed as a product. Even while a certain salt form may provide desirable qualities in one aspect, for example the manufacturing process, its selection must still be assessed in view of its other qualities (e.g. pharmacokinetic properties). An example of a pharmacologically acceptable salt is alfadolone acetate, which is encompassed by the present disclosure. An example of a derivative of a neuroactive steroid anaesthetic is a deuterated or tritiated derivative as well as a derivative encompassed by Formula X, including alfaxalone, alfadolone and alfadolone acetate. A "modified" cyclodextrin includes a derivative of a cyclodextrin.

The neuroactive steroids prepared by the methods described herein may be in the form of an anaesthetic or sedating composition or as a non-sedating analgesic or neuroprotectant composition. Accordingly, in another aspect of the present invention, pharmaceutically acceptable compositions are provided, wherein these compositions comprise a neuroactive steroid prepared by the methods described herein, and optionally comprise a pharmaceutically acceptable carrier, adjuvant or vehicle. In certain embodiments, these compositions optionally further comprise one or more additional therapeutic agents.

Further taught herein are methods for inducing anaesthesia or sedation in a subject comprising administering to the subject an effective amount of a neuroactive steroid prepared by the methods described herein. It is also envisaged that compositions of the neuroactive steroids prepared by the methods described herein can also initiate rapid induction of anaesthesia to surgical levels with similar or more rapid wakening time compared to propofol without long term neuronal dysfunction.

Such compositions may be for in vivo delivery meaning that the neuroactive steroid is delivered by intravenous, sub-cutaneous, intraperitoneal, intrathecal, intramuscular, intravitreal, transdermal, suppository (rectal), pessary (vaginal), inhalation, intranasal and the like. Most effectively, the formulation is an intravenous (iv) formulation. Alfadolone given orally is non-sedating and induces analgesia alone or in combination with an opioid. In one or more embodiments, the compositions may be formulated for delivery via a subcutaneous or intramuscular depot, implant, pellet or similar delivery device. In or more embodiments, it is envisaged that such a device may provide a controlled rate of delivery over a prolonged period of time.

Compositions comprising the neuroactive steroids prepared by the methods described herein may include one or more pharmaceutically acceptable carriers. Cyclodextrins form a useful carrier in the formulation of the neuroactive steroids, however, other carriers may also be used such as polyethoxylated castor oil (CremophorEL).

Compositions comprising the neuroactive steroids prepared by the methods described herein may in an embodiment comprise a buffer such as a phosphate or tris or citrate phosphate buffer to maintain the pH from about 5.5 to about pH 8. This includes pH values of 5.5, 6, 6.5, 7, 7.5 and 8. Alternatively, the composition does not comprise a buffer and the pH being from about pH 3 to about pH 9.5 such as pH 3, 3.5, 4, 4.5, 5, 5.5, 6, 6.5, 7, 7.5, 8, 8.5, 9 or 9.5.

In a further aspect, the compositions comprising the neuroactive steroids prepared by the methods described herein may also include one or more agents such as excipients, preservatives, and/or microbial retardants. Other agents may also be included to reduce toxicity. Agents include, for example, EDTA, benzyl alcohol, chlorocresol, bisulphites, monoglyceryl ester of lauric acid (Monolaurin), capric acid and/or its soluble alkaline salts or its monoglyceryl ester (Monocaprin), edetate, and capric acid and/or its soluble alkaline salts or its monoglyceryl ester (Monocaprin) and edetate. The formulation may also contain one or more co-polymers to assist in solubility or stability of the anaesthetic agent. Examples include hydroxy propyl methyl cellulose (HPMC), polyvinyl pyrrolidone (PVP) and/or carboxymethyl cellulose (CMC).

Conveniently, the neuroactive steroid anaesthetic is provided at a concentration of from about 0.5 to 100 mg/ml in a saline or water suspension comprising the cyclodextrin. Such a concentration includes 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 mg/ml of drug. As indicated above, the composition is generally formulated so that the molar ratio of neuroactive steroid to cyclodextrin is from about 1:1 to about 1:6, including from about 1:1 to 1:4, including from about 1:1 to 1:3 and including about 1:2. For alfadolone, the molar ratio is from 1:2 to 1:6.

The present disclosure is instructional for a method of inducing analgesia in a subject, the method comprising administering to the subject an effective amount of a neuroactive steroid prepared by the methods described herein.

The amount of a neuroactive steroid included in a composition will be determined by the nature of the animal to be treated. In an embodiment, a level of 1-100 mg/mL, including 5-25 mg/mL, including 7-15 mg/mL may be appropriate.

Another aspect enabled herein is directed to a drug delivery host/guest composition comprising a cyclodextrin host or modified form thereof with a neuroactive steroid anaesthetic steroid guest prepared by the methods described herein. Particular examples include alfaxalone, alfadolone and pharmacologically and pharmaceutically acceptable derivatives, salts and pro-drug forms thereof.

In an embodiment, the neuroactive steroid is formulated in a cyclodextrin and is provided in an amount of from about 0.001 mg/kg to about 20 mg/kg/body weight per hour.

The neuroactive steroids prepared by the methods described herein may also be administered with an opioid in order to facilitate analgesia without adverse neurological symptoms developing. Alternatively, the neuroactive steroid is co-formulated or otherwise administered sequentially or simultaneously.

The neuroactive steroids prepared by the methods described herein may be administered with another drug such as a cholesterol lowering drug including a statin (e.g. atorvastatin) to avoid neuronal dysfunction (e.g. cognitive decline).

Therapeutic kits comprising the neuroactive steroids prepared by the methods described herein, packaged for sale or use by a clinician are also taught herein. In some embodiments, the kit may be packaged for sale or use by a suitable healthcare professional including a doctor, nurse, paramedic, veterinarian, and the like. The kit may further contain an analgesic, or a neurological drug.

Whilst the present disclosure teaches anaesthetic formulations for use in humans, the formulations may also be used in animals such as for clinical trials or veterinary use. Non-human animals contemplated herein include rats, mice, guinea pigs, hamsters, sheep, pigs, dogs, cats, horses, cows, goats, camels and non-human primates.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

The following examples are intended to illustrate the invention are not to be construed as being limitations thereon. The following reactions may be performed on a milligram, gram or kilogram scale.

Methods of Analysis

High-Performance Liquid Chromatography (HPLC)

HPLC analysis was carried out on a Varian 1100 series HPLC with diode array detection; indicating 99.8% purity. Analysis conducted with a silica gel column, SILIACHROM® dtC18, 5 µm, 100 Å, 4.6×250 mm, column at 205 and 235 nm, elution conducted using a gradient system of 40% acetonitrile to 90% acetonitrile in water at 1 ml/min for 26 minutes. Samples were prepared according to the British Pharmacopoeia at 0.2% (w/v) using betamethasone as internal standard.

Fourier Transform Infrared Spectroscopy (FT-IR)

Infrared spectroscopy was carried out on spectrometer endowed with an ATR module, using a resolution of 4 cm$^{-1}$. The spectrum was recorded between 4000 and 600 cm$^{-1}$.

$^1$H- and $^{13}$C-Nuclear Magnetic Resonance Spectroscopy ($^1$H-NMR, $^{13}$C-NMR)

$^1$H- and $^{13}$C-Nuclear Magnetic Resonance measurements were recorded on a Varian VNMRS instrument at 500 MHz and 125 MHz respectively, and room temperature using CDCl$_3$ as solvent without an internal standard.

19
Synthetic Methods

A representative synthesis corresponding to Examples 1 to 5 is shown in Scheme 7 below:

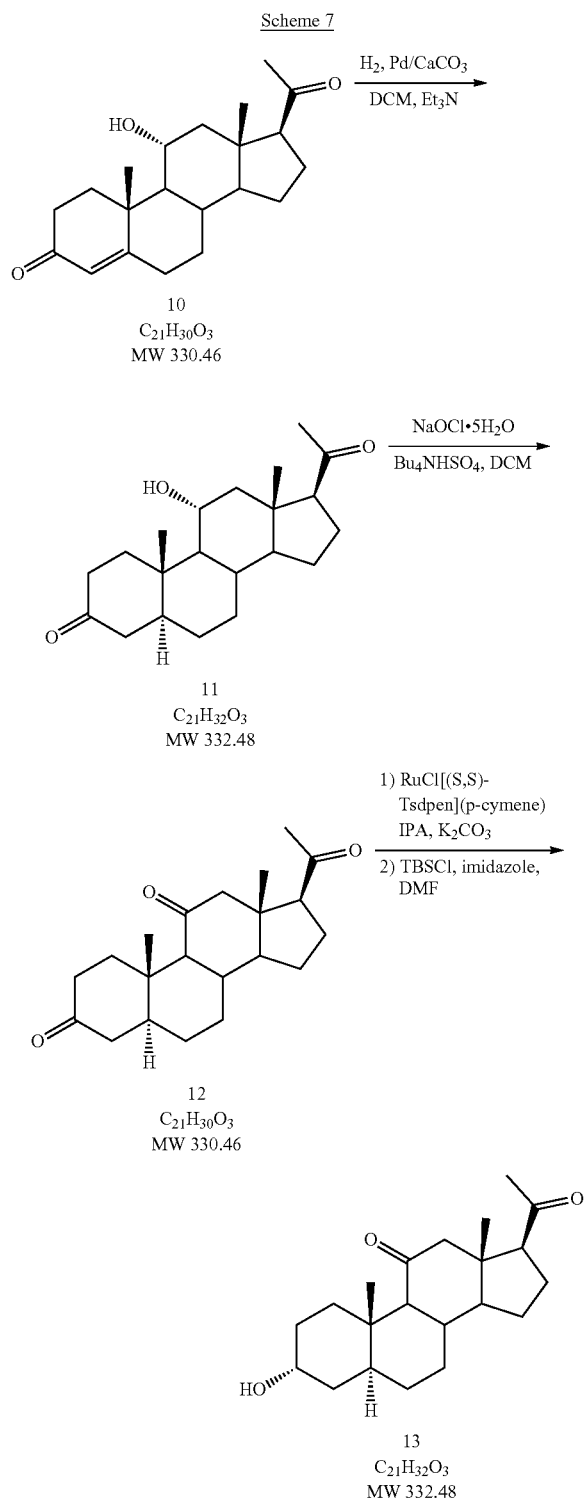

Representative synthesis of compounds of Formula (I)

20
Example 1

Hydrogenation of 11α-hydroxyprogesterone (10) to 11α-hydroxy-3,20-diketo-5α-H pregnane (11)

11α-hydroxyprogesterone (10) (250.0 g, 756.5 mmole) was dissolved in methylene chloride (3.92 L) and triethylamine (83 ml, 595.1 mmole). The catalyst, 5% Pd/CaCO$_3$ (22.50 g, 1.125 g Pd, 0.5 wt %) was added, the 10 L reactor was purged alternatively with nitrogen/vacuum 4 times, then with hydrogen/vacuum 4 times. Hydrogenation was carried out at 100 psi hydrogen and at 30° C. A very fast uptake occurred over 24 minutes, followed by a slower uptake over 2 hours. Total uptake was calculated to be 1.00 eq. of hydrogen. Workup of the reaction was carried out at 3 hours, after cooling to 20° C., purging with nitrogen/vacuum, and emptying the reaction contents (with washing with methylene chloride) into a container. The slurry was filtered to remove the catalyst with another 1 L methylene chloride wash. The total methylene chloride filtrate (5.3 L) was extracted with 500 ml of 1.5M HCl, and then with 500 ml of 10% potassium bicarbonate. The two separate aqueous layers were re-extracted with 1 L methylene chloride. The final methylene chloride was dried over magnesium sulfate, filtered (and washed) and vacuum concentrated to dryness to give a white solid, wt. 252.4 g. This material was slurried with MTBE (1.25 L) at 50° C. for 2 hours, then at 20° C. for 1 hour. The crystalline slurry was filtered and dried to give 173.66 g of a white solid. The HPLC assay of 11α-hydroxy-3,20-diketo-5H-pregnane showed 0.548% polar imp., 95.553% desired 5α-H product, and 3.899% of the 5β-H product (corresponding to a ratio of 96.08:3.92 of 5αH:5βH).

The product was resuspended in MTBE (700 ml) and stirred at 50° C. for 2 hours, and 1 hour at 25° C. Filtration, washing, and drying gave 170.3 g of purified product, but the HPLC showed only a very small change in the 5αH:5βH ratio (96.64:3.37).

The solid (167.76 g) was dissolved in acetonitrile (2.1 L) at 70° C. The clear colourless solution was slowly cooled. At 65° C., seeds of the product from a small scale crystallization were added and they did not dissolve. The mixture was cooled at a rate of 10° C. every 45 minutes to a final temperature of 5° C. The slurry was stirred for ca 1-2 hours, filtered, and washed with cold acetonitrile and dried overnight to give 11α-hydroxy-3,20-diketo-5α-H-pregnane (140.76 g, 423 mmol, 56%). $^1$H- and $^{13}$C-NMR consistent with desired product. HPLC showed 99.558% of the desired 5αH isomer and 0.442% of the unwanted 5βH isomer. Pd assay <1 ppm. NMR and HPLC results were compared to authentic samples of 5α and 5β isomers purchased from Steraloids.

Figure 7:
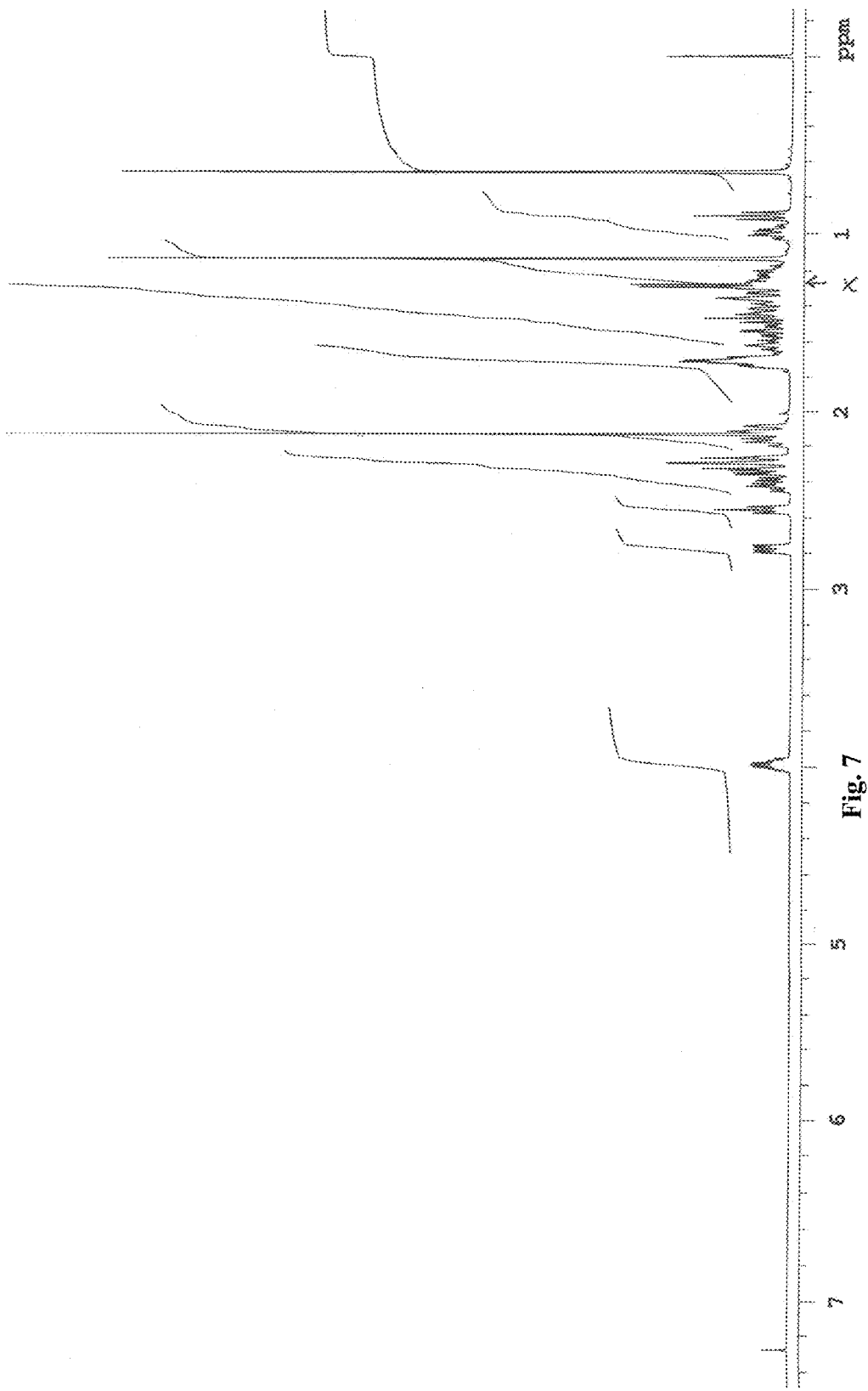
FIG. 7: $^1$H NMR spectrum of 11α-hydroxy-3,20-diketo-5α-H-pregnane; at 25° C. in CDCl$_3$.
Figure 8:
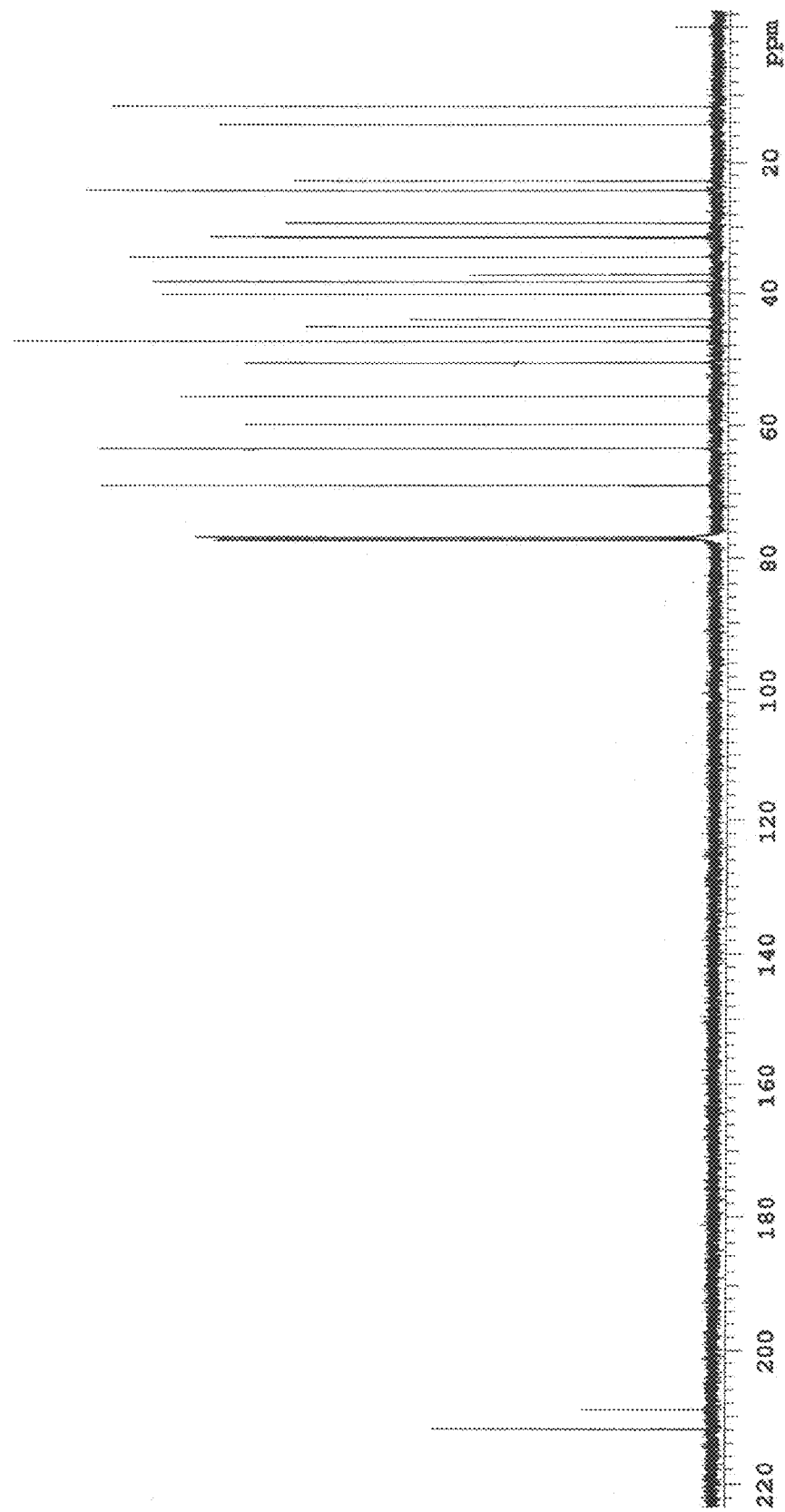
FIG. 8: $^{13}$C NMR spectrum of 11α-hydroxy-3,20-diketo-5α-H-pregnane; at 25° C. in CDCl$_3$.

$^1$H NMR and $^{13}$C NMR spectra of 11α-hydroxy-3,20-diketo-5α-H pregnane; at 25° C. in CDCl$_3$ are shown in FIGS. 7 and 8.

Example 2

Oxidation of 11α-hydroxy-3,20-diketo-5α-H-pregnane (11) to 3,11,20-triketo-5α-H-pregnane (12)

To 11α-hydroxy-3,20-diketo-5α-H-pregnane (100 g, 301 mmol) tetrabutylammonium hydrogensulfate (10 g, 30 mmol) in DCM (1 L) at 21° C. was added NaOCl.5H$_2$O (87.9 g, 535 mmol) in portions over 4.5 hours keeping the temperature between 20 and 24° C. The reaction was cooled to 12° C. then quenched by addition of cold 0.24M Na$_2$S$_2$ O₃ (460 ml). The layers were separated and the aqueous re-extracted with DCM (300 ml). The combined organic layers were dried over MgSO₄ (30 g) and silica (50 g), filtered and washed with DCM (200 ml). The filtrate was partially concentrated to 410 g solution. This was loaded on to a 1 kg silica column and eluted with 2-20% EtOAc in DCM collecting 1 L fractions. The higher purity product fractions were concentrated to a solid (51 g wet weight). This was triturated in MeCN (250 ml) at 55° C. for 25 minutes then 28 ml of solvent was distilled under vacuum to remove residual DCM. The slurry was cooled to 0° C., filtered and washed with cold MeCN (55 ml) to afford a white solid (45.77 g, ~96% purity by ¹H-NMR).

Other fractions where concentrated and combined, and where required triturated or chromatographed to provide a white solid. ¹H-NMR of the resultant solid was consistent with desired product in high purity (compared to authentic sample purchased from Steraloids). Total yield=50.2 g, 152 mmol, 51% yield.

Figure 9:
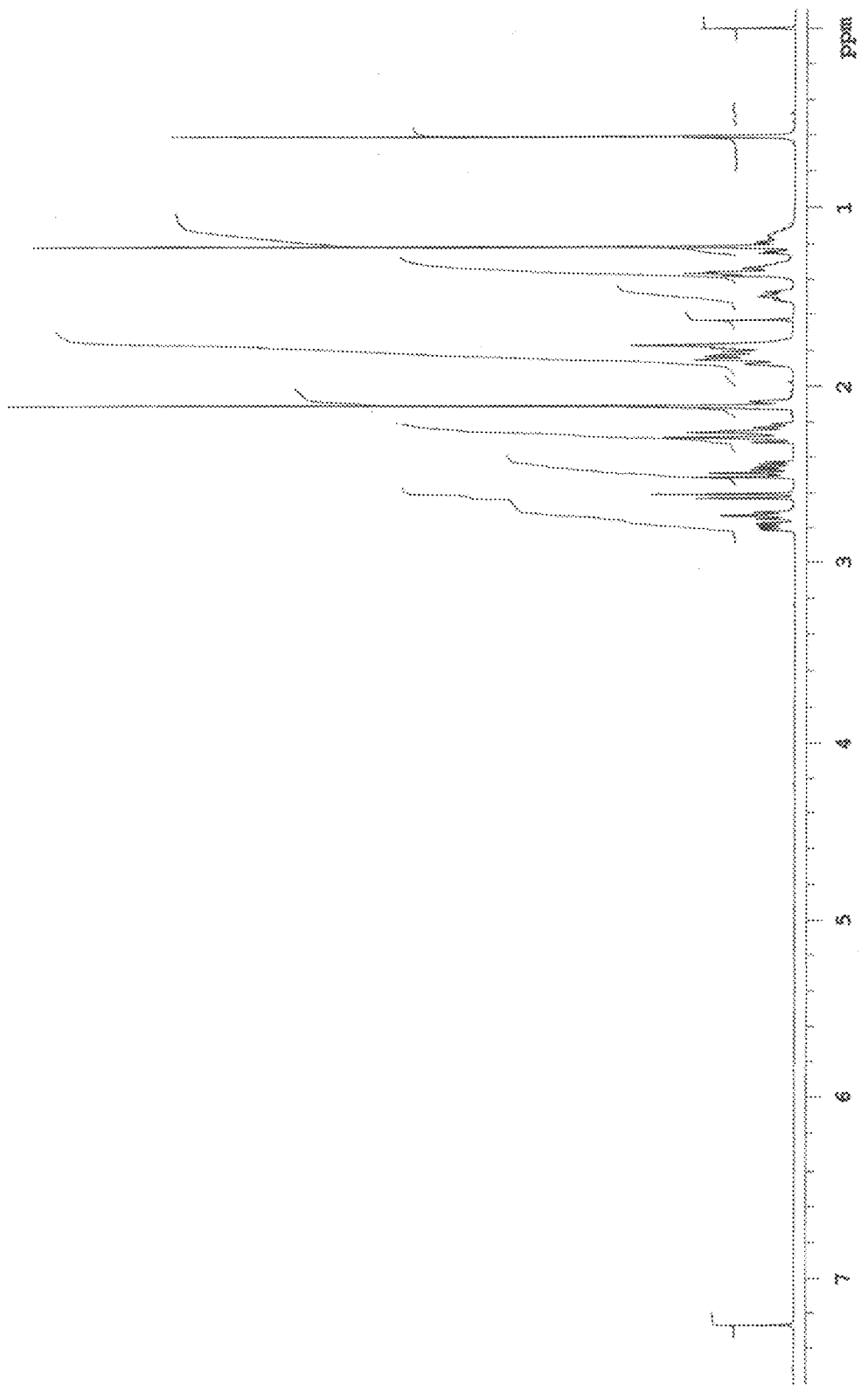
FIG. 9: $^1$H NMR spectrum of 3,11,20-triketo-5α-H-pregnane; at 25° C. in CDCl$_3$.

¹H NMR spectrum of 3,11,20-triketo-5α-H-pregnane; at 25° C. in CDCl₃ is shown in FIG. 9.

Example 3

Reduction of 3,11,20-triketo-5α-H-pregnane (12) to alfaxalone, 3α-hydroxy-5α-pregnane-11,20-dione (13)

3,11,20-triketo-5α-H-pregnane and potassium hydrogen carbonate were dissolved in ethanol and de-oxygenated, then RuCl[(S,S)-Tsdpen](p-cymene) was added. The mixture was warmed to 56° C. for 20 hours. The mixture was filtered and evaporated to afford crude 3α-hydroxy-5α-pregnane-11,20-dione. The reaction proceeded with high regioselectivity (reduction of 11 and 20 ketones was not detected) and ~80:20 stereoselectivity 3αOH:3βOH. This surprising result removed the need for protecting groups and simplified the overall synthesis of alfaxalone (3α-hydroxy-5α-pregnane-11,20-dione).

Example 4

Optimization of 3,11,20-triketo-5α-H-pregnane (12) reduction to alfaxalone, 3α-hydroxy-5α-pregnane-11,20-dione (13)

Optimization of the ruthenium-catalyzed reduction of 3,11,20-triketo-5α-H-pregnane was conducted (Refer to Table 1). A number of ruthenium catalysts provided regioselective reduction and/or stereoselective reduction of 3,11,20-triketo-5α-H-pregnane. RuCl(p-cymene)[(S,S)-Tsdpen] provided the best regio- and stereo-selectivity. Use of KHCO₃ in methanol or K₂CO₃ in IPA both gave slightly improved selectivity. K₂CO₃ in IPA provided a slightly cleaner reaction with regards to formation of other by-products.

TABLE 1

Optimization of ruthenium catalyzed reduction

| Entry | Catalyst | Solvent | Base | Conditions | Result |
|---|---|---|---|---|---|
| 1 | RuCl(p-cymene)[(S,S)-Tsdpen] | Ethanol | KHCO₃ | 56° C., 20 hours | NMR ~4:1 α:β |
| 2 | RuCl(p-cymene)[(R,R)-Tsdpen] | Ethanol | KHCO₃ | 56° C., 20 hours | NMR ~2:1 α:β |
| 3 | RuCl(p-cymene)[(S,S)-Tsdpen] | Ethanol | KHCO₃ | 50° C., 16 hours | NMR ~4:1 α:β |
| 4 | RuCl(mesitylene)[(S,S)-Tsdpen] | Ethanol | KHCO₃ | 50° C., 16 hours | NMR ~3:2 α:β |
| 5 | RuCl(p-cymene)[(S,S)-Fsdpen] | Ethanol | KHCO₃ | 50° C., 16 hours | NMR ~4:1 α:β |
| 6 | RuCl[(S,S)-Ms-DENEB] | Ethanol | KHCO₃ | 50° C., 16 hours | NMR ~2:1 α:β |
| 7 | RuCl(p-cymene)[(S,S)-Tsdpen] | Methanol | KHCO₃ | 48° C., 16 hours | HPLC 85.8:14.2 α:β |
| 8 | RuCl(p-cymene)[(S,S)-Tsdpen] | Methanol | K₂CO₃ | 48° C., 1 hour | TLC/NMR showed more by-products; α:β ratio not measured. |
| 9 | RuCl(p-cymene)[(S,S)-Tsdpen] | Ethanol | KHCO₃ | 48° C., 16 hours | HPLC 82.2:17.8 α:β |
| 10 | RuCl(p-cymene)[(S,S)-Tsdpen] | Ethanol | K₂CO₃ | 48° C., 1 hour | TLC/NMR showed more by-products; α:β ratio not measured. |
| 11 | RuCl(p-cymene)[(S,S)-Tsdpen] | IPA | KHCO₃ | 48° C., 16 hours | HPLC 80.5:19.5 α:β |
| 12 | RuCl(p-cymene)[(S,S)-Tsdpen] | IPA | K₂CO₃ | 48° C., 1 hour | HPLC 84.3:15.7 α:β |

It was advantageously found that the 3βOH isomer exhibited differing reactivity with bulky silylating agent TBSCl. As such, the 3αOH and 3βOH were separated by selective reaction of the 3βOH with TBSCl to take advantage of the difference in reactivity of the axial and equatorial alcohols. These conditions left the 3αOH largely unprotected. The protected 3β-OTBS was then removed by chromatography.

Example 5

Ruthenium Reduction of 3,11,20-triketo-5α-H-pregnane (12) reduction to alfaxalone, 3α-hydroxy-5α-pregnane-11,20-dione (13)

3,11,20-triketo-pregnane (151 mmol) and potassium carbonate (12.5 g, 90.6 mmol) in IPA (750 ml) was deoxygenated with 3×vacuum/nitrogen cycles at 19° C. RuCl [(S,S)-Tsdpen](p-cymene) (2.19 g, 3.44 mmol) was added, and an additional vacuum/nitrogen cycle was performed. The mixture was warmed to 26 to 27° C. for 16 hours (monitored by HPLC). The mixture was treated with magnesol (50 g), silica (50 g) and carbon (1.7 g) for one hour while cooling to 23° C. then filtered through a pad of Celite, rinsing with IPA. The filtrate was evaporated and the residue azeotroped with heptane to afford crude 3α/3β-hydroxy-5α-pregnane-11,20-dione (51.1 g).

To crude 3α/3β-hydroxy-5α-pregnane-11,20-dione (51.1 g) and imidazole (4.0 g, 59 mmol) in DMF (400 ml) at −7° C. was added TBSCl (5.50 g, 36.5 mmol). The mixture was gradually warmed to −1° C. over 2 hours and then to +2° C. over 35 mins (HPLC—1.51% 3β-OH). The mixture was re-cooled to −6° C. and additional TBSCl (1.45 g, 9.6 mmol) was added. The mixture was allowed to gradually warm to +4° C. over 1.5 hours (HPLC—0.47% 3β-OH) and then quenched by addition of cold water (1.2 L). The resulting slurry was filtered and washed with water. The wet solids were dissolved in DCM (200 ml) and the small residual water layer was separated and re-extracted with DCM (50 ml). The combined organics were dried over MgSO$_4$ and magnesol (6 g each), filtered and the solids were washed with DCM (50 ml). The filtrate was stirred with SiliaMetS Thiol resin (15 g, 1.31 mmol/g loading) at 22° C. for 3.5 hours then filtered and washed with DCM (50 ml). The filtrate was evaporated to afford 53 g of a pale tan solid. Chromatography (2.5 kg silica, 5 to 30% EtOAc) afforded 31.95 g of product as a white solid.

The solid was dissolved in IPA (165 ml) at 65° C. then water (330 ml) was added over 80 mins, keeping temp >59° C. The resulting slurry was cooled to 15° C. over 2 hours, filtered and washed with 3:1 water:IPA (40 ml) then water (90 ml). The solids were dried under vacuum at 60° C. to afford alfaxalone (30.7 g, 92.3 mmol, 61%) as a white solid. Analytical information was compared to authentic samples of 3α and 3β isomers purchased from Steraloids (Newport, R.I., USA 02840).

Figure 2:
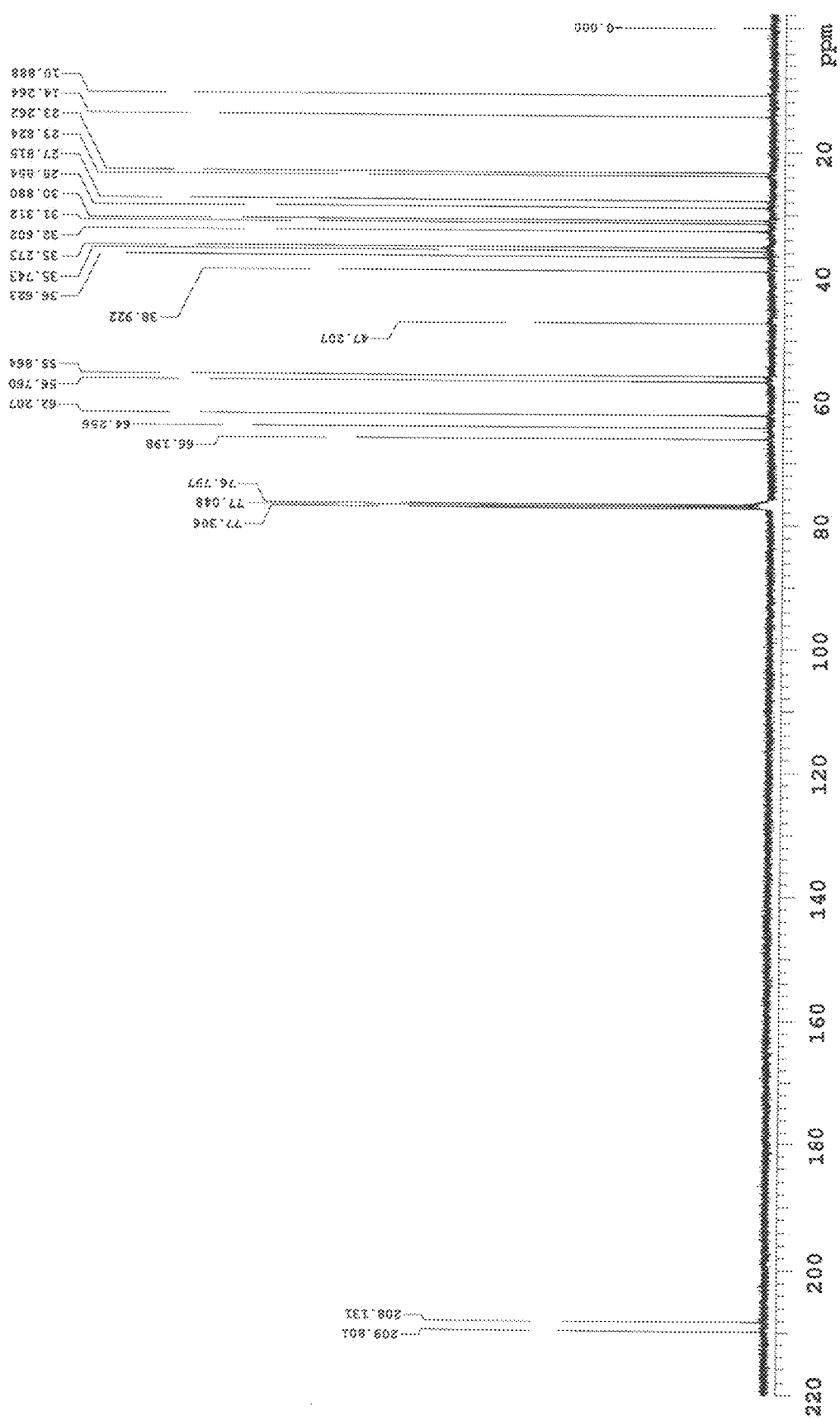
FIG. 2: $^{13}$C NMR spectrum of alfaxalone (3α-hydroxy-5α-pregnane-11,20-dione) prepared by the methods of the invention; at 25° C. in CDCl$_3$.
Figure 3:
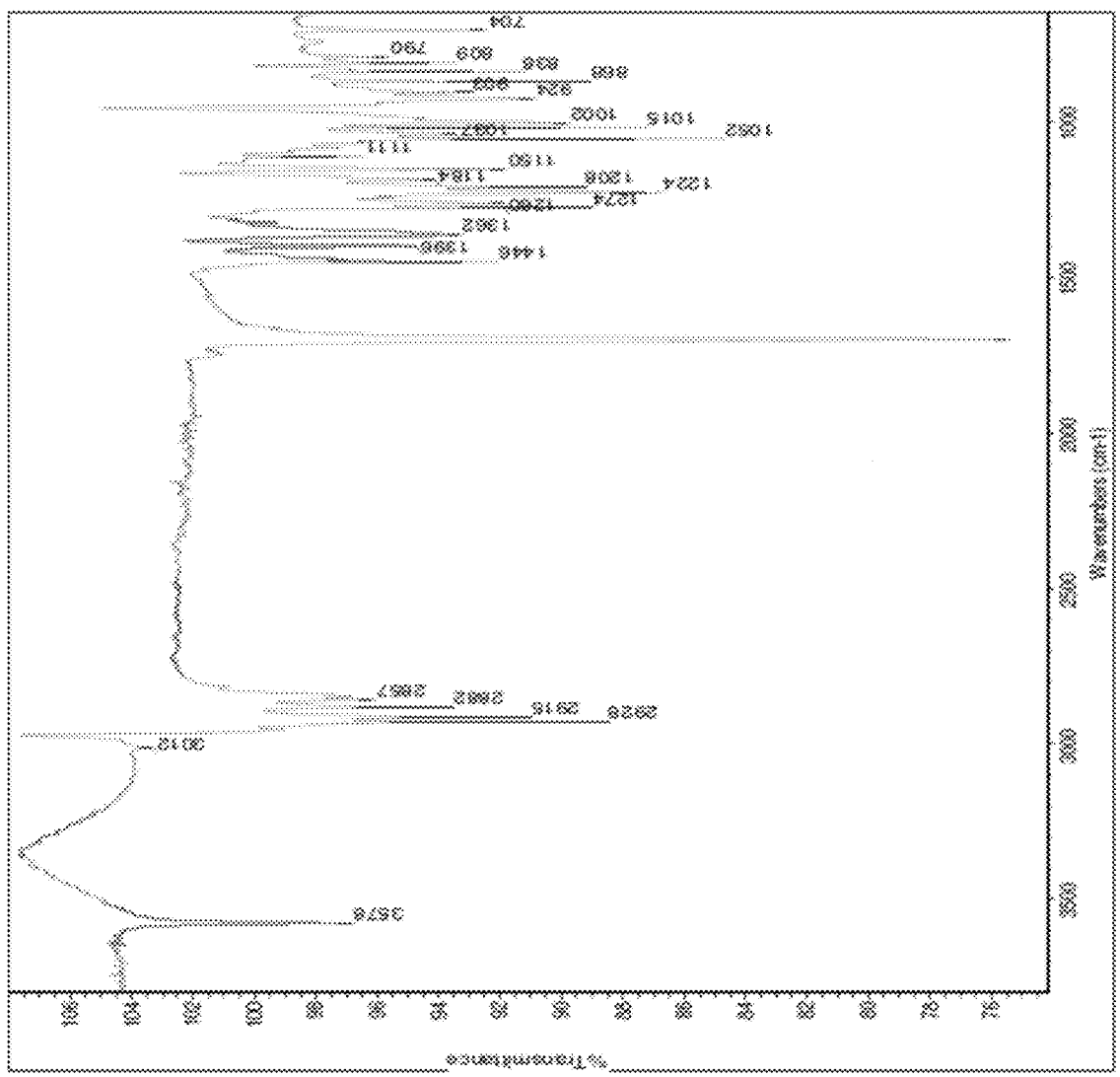
FIG. 3: IR spectrum of alfaxalone (3α-hydroxy-5α-pregnane-11,20-dione) prepared by the methods of the invention.
Figure 4:
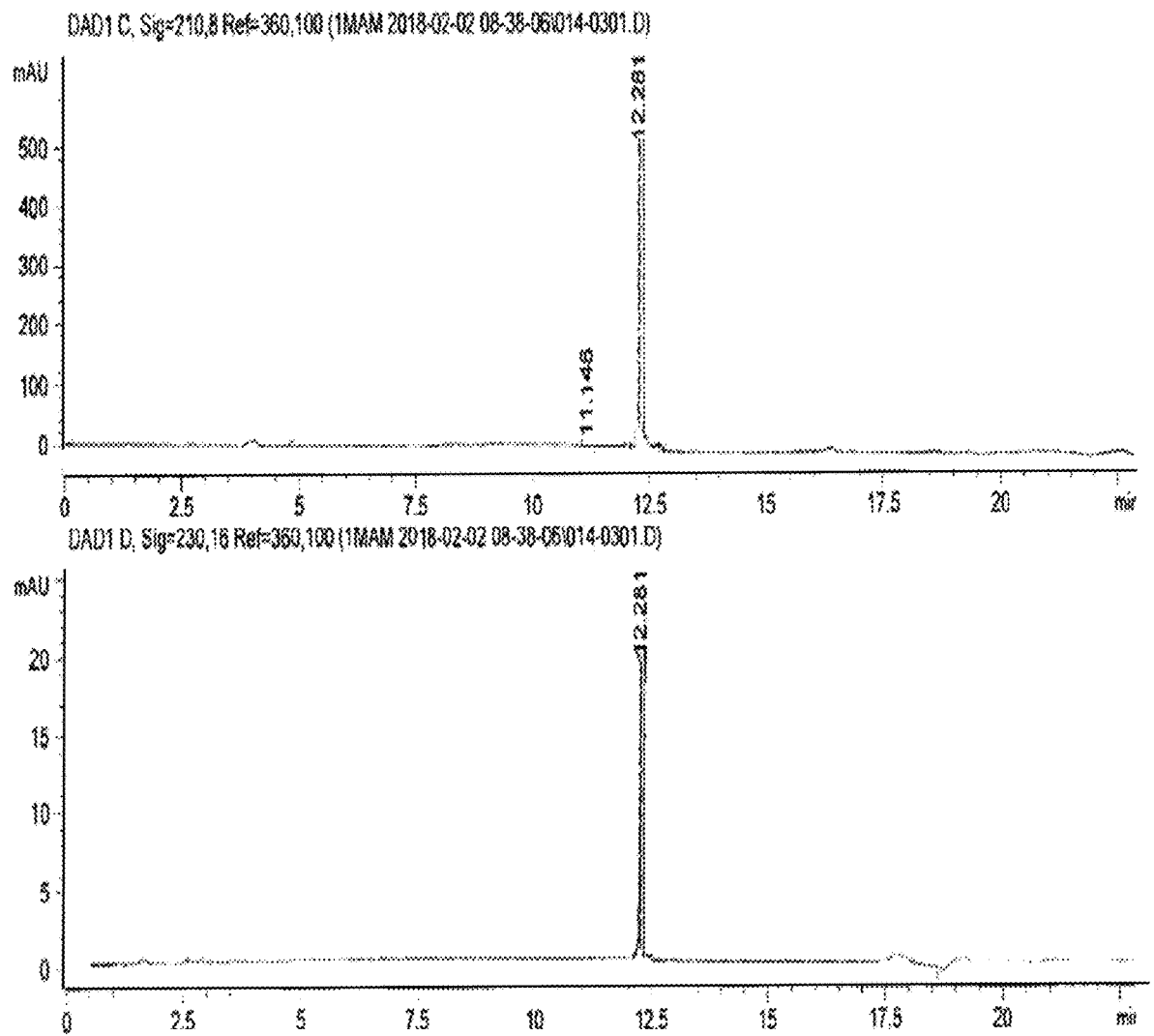
FIG. 4: HPLC analysis of alfaxalone (3α-hydroxy-5α-pregnane-11,20-dione) prepared by the methods of the invention using a Varian 1100 series HPLC with diode array detection; indicating 99.8% purity. Analysis conducted with a silica gel column, SILIACHROM® dtC18, 5 μm, 100 Å, 4.6×250 mm, column at 205 and 235 nm, elution conducted using a gradient system of 40% acetonitrile to 90% acetonitrile in water at 1 ml/min for 26 minutes. Samples were prepared according to the British Pharmacopoeia at 0.2% (w/v) using betamethasone as internal standard.
Figure 5:
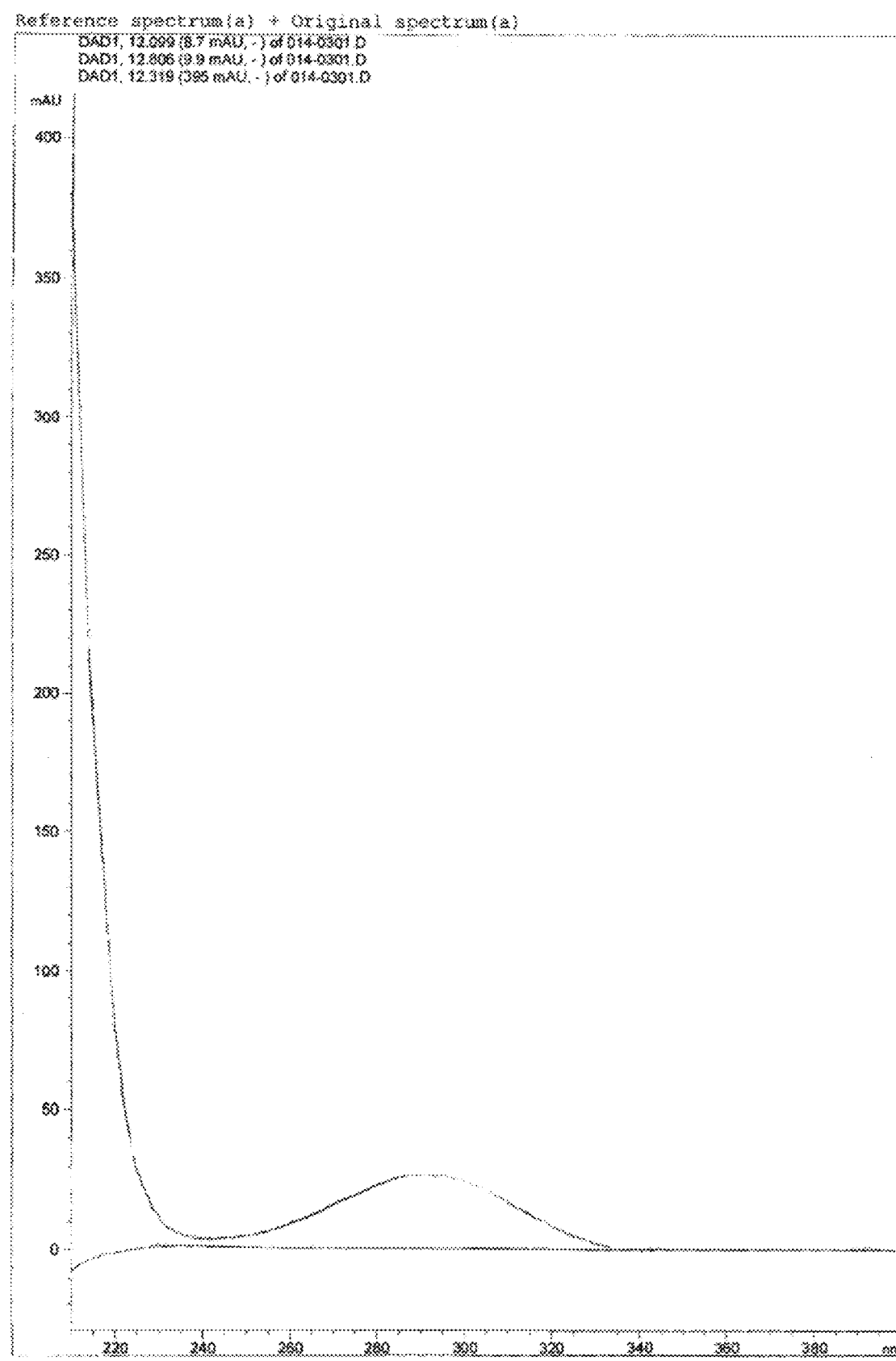
FIG. 5: UV-vis spectrum of alfaxalone (3α-hydroxy-5α-pregnane-11,20-dione) prepared by the methods of the invention.
Figure 6:
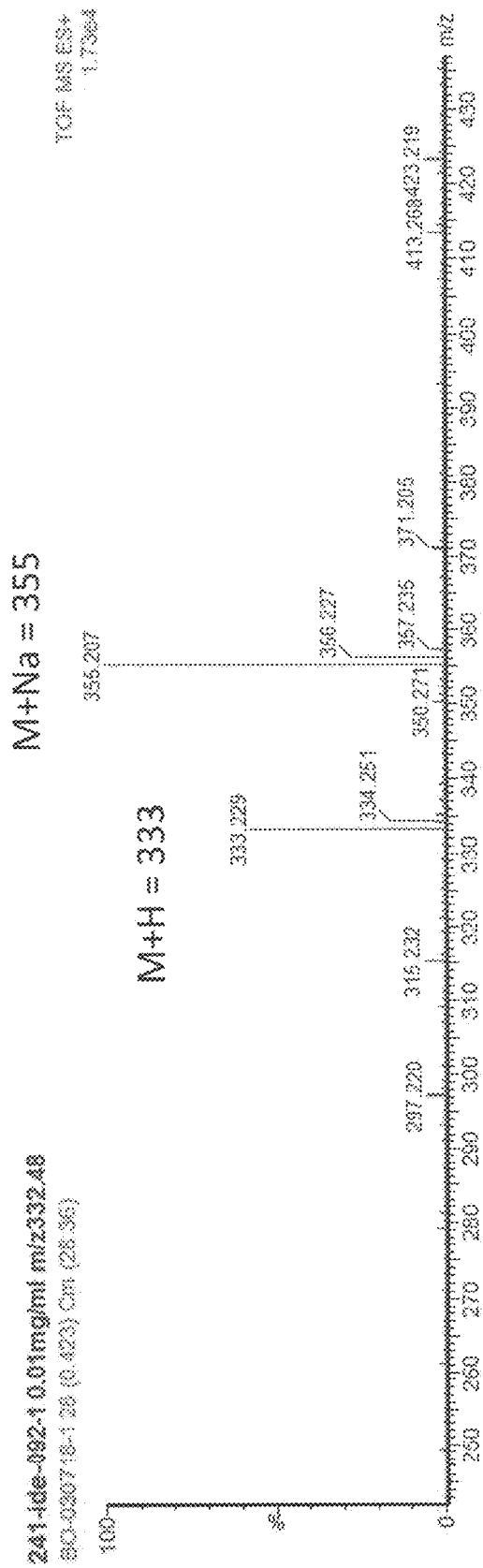
FIG. 6: Mass spectra of alfaxalone (3α-hydroxy-5α-pregnane-11,20-dione).

$^1$H NMR and $^{13}$C NMR spectra of alfaxalone (3α-hydroxy-5α-pregnane-11,20-dione) are shown in FIGS. 1 and 2; IR spectrum of alfaxalone is shown in FIG. 3; HPLC analysis is shown in FIG. 4; UV-vis spectrum is shown in FIG. 5 and mass spectrum is shown in FIG. 6.

This process resulted in a higher yield of alfaxalone than that obtained in the prior art, such as in U.S. Pat. No. 3,714,352 and/or Browne, P. A.; Kirk, D. N.: *J. Chem Soc* (JCSA9) 1969, p. 1653.

Example 6

Synthesis of Alfadolone Acetate (14) and Alfadolone (15) from Alfaxalone

It is generally recognised that alfaxalone (3α-hydroxy-5α-pregnane-11,20-dione) may be elaborated to alfadolone acetate and alfadolone by previously described methods, as detailed in Scheme 3.

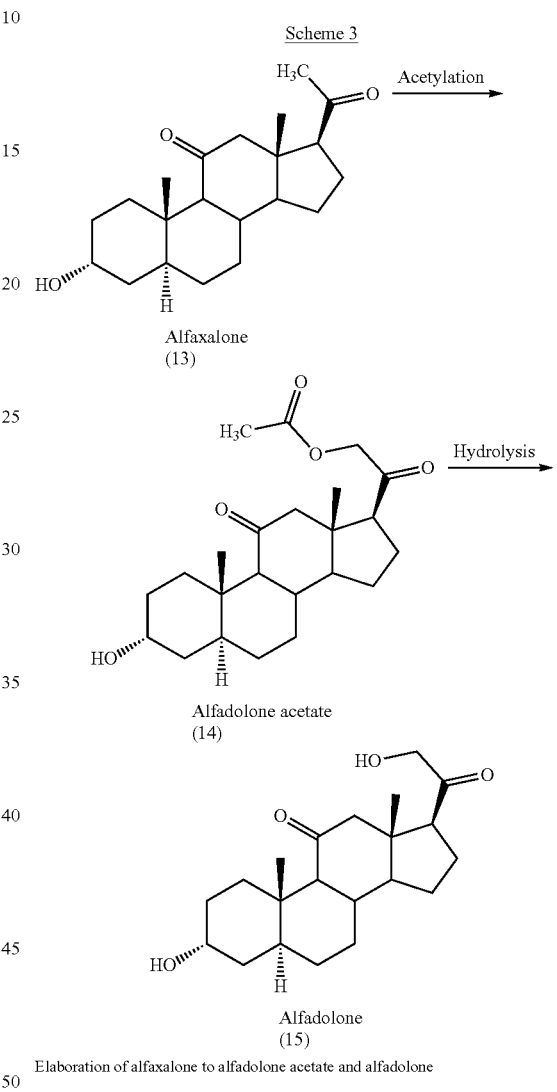

Scheme 3

Alfaxalone (13)

Alfadolone acetate (14)

Alfadolone (15)

Elaboration of alfaxalone to alfadolone acetate and alfadolone

Addition of lead tetraacetate and boron trifluoride etherate to alfaxalone provides alfadolone acetate. Alternatively, addition of bromine in ethanol affords 21-bromoalfaxalone which may be further elaborated to alfadolone acetate by addition of potassium acetate in acetone. Examples of suitable synthetic methods are described in DE 2 030 402, ZA 703 861 and Browne, P. A.; Kirk, D. N.: *J. Chem Soc* (JCSA9) 1969, p. 1653, the entire contents of which are incorporated herein by reference.

Alfadolone may be accessed by hydrolysis (or deacetylation) of alfadolone acetate under standard conditions, such as the addition of K$_2$CO$_3$ in MeOH. For other examples of suitable conditions refer to T. W. Green, P. G. M. Wuts, *Protective Groups in Organic Synthesis*, Wiley-Interscience, New York, 1999, 150-160, 712-715, incorporated herein by reference.

What is claimed is:

1. A process for preparing a compound of Formula (I)

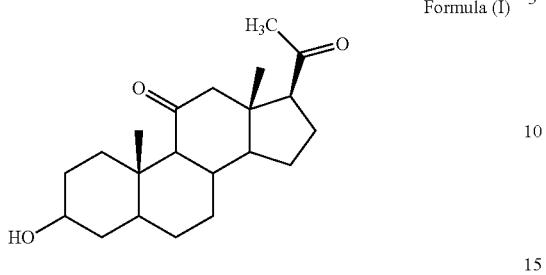
Formula (I)

comprising a ruthenium-catalyzed reduction of the 3-ketone of compound of Formula (II)

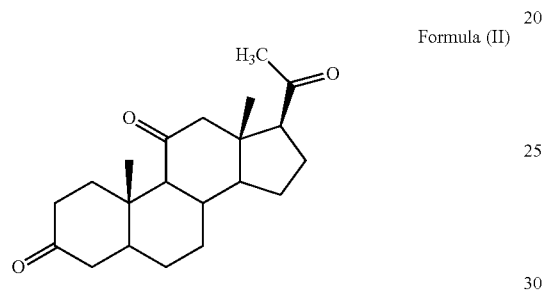
Formula (II)

to provide a compound of Formula (I).

2. The process according to claim 1, wherein the reduction provides ≥80:20 stereoselectivity 3α-hydroxy:3β-hydroxy of Formula (I).

3. The process according to claim 1, wherein the compound of Formula (I) is 3α-hydroxy-5α-pregnane-11,20-dione of Formula (Ia)

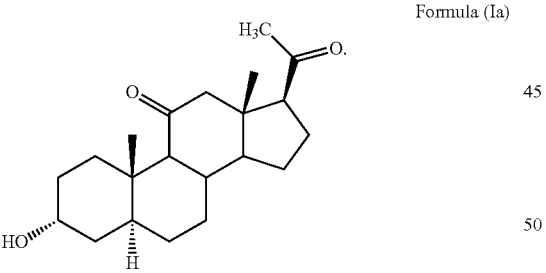
Formula (Ia)

4. The process according to claim 1, wherein the ruthenium catalyst is selected from the group consisting of RuCl(p-cymene)[(R,R)-Tsdpen], RuCl(p-cymene)[(S,S)-Tsdpen], RuCl(mesitylene)[(S,S)-Tsdpen], RuCl(p-cymene)[(S,S)-Fsdpen], and RuCl[(S,S)-Ms-DENEB].

5. The process according to claim 1, comprising mixing a compound of Formula (II) with a carbonate salt in an organic solvent.

6. The process according to claim 5, wherein the carbonate salt is potassium hydrogen carbonate or potassium carbonate.

7. The process according to claim 5, wherein the organic solvent is isopropyl alcohol.

8. The process according to claim 3, further comprising
i) reduction of 11α-hydroxyprogesterone of Formula (III)

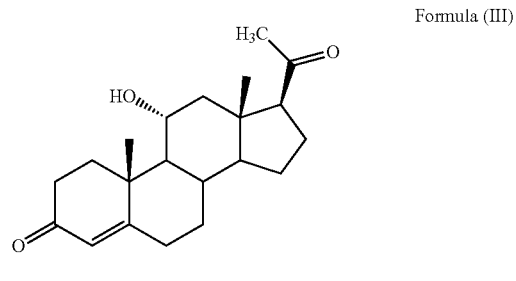 [SMILES: CC(=O)[C@H]1CCC2C3CCC4=CC(=O)CC[C@]4(C)C3[C@H](O)C[C@@]21C]
Formula (III)

to provide 11α-hydroxy-3,20-diketo-5α-H-pregnane of Formula (IV)

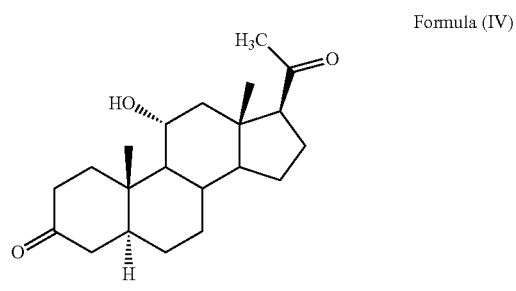 [SMILES: CC(=O)[C@H]1CCC2C3CC[C@H]4CC(=O)CC[C@]4(C)C3[C@H](O)C[C@@]21C]
Formula (IV)

ii) oxidation of 11α-hydroxy-3,20-diketo-5α-H-pregnane of Formula (IV) to provide 3,11,20-triketo-5α-H-pregnane of Formula (II)

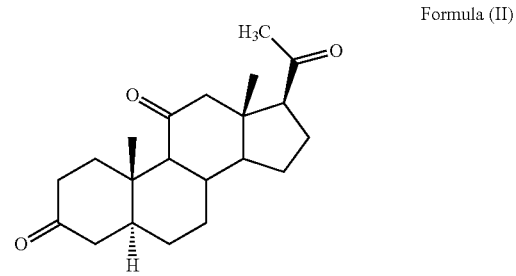 [SMILES: CC(=O)[C@H]1CCC2C3CC[C@H]4CC(=O)CC[C@]4(C)C3C(=O)C[C@@]21C]
Formula (II)

iii) reduction of 3,11,20-triketo-5α-H-pregnane of Formula (II) to provide a compound of Formula (Ia).

9. The process according to claim 8, wherein the reduction at step i) is a palladium catalyzed hydrogenation.

10. The process according to claim 9, wherein the palladium catalyst is Pd/CaCO$_3$.

11. The process according to claim 9, wherein the hydrogenation further comprises an organic solvent.

12. The process according to claim 11, wherein the organic solvent is dicholoromethane, dicholoromethane/trimethylamine, or dichloromethane/triethylamine.

13. The process according to claim 8, wherein the oxidation at step ii) comprises addition of NaOCl and a phase transfer catalyst.

14. The process according to claim 13, wherein the phase transfer catalyst is tetrabutylammonium hydrogen sulfate.

15. The process according to claim 3, further comprising iv) hydroxylation of a compound of Formula (Ia)

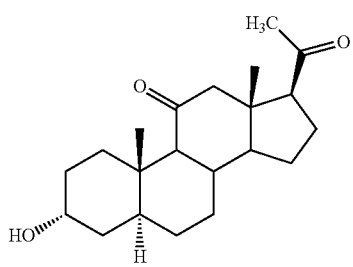 Formula (Ia)
to provide a compound of Formula (V)
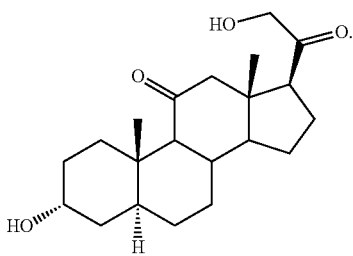 Formula (V)
16. The process according to claim 3, further comprising
iv) acetylation of a compound of Formula (Ia)
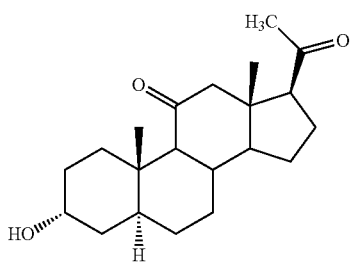 Formula (Ia)
to provide a compound of Formula (VI)
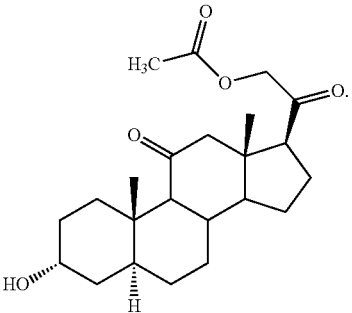 Formula (VI)
* * * * *